United States Patent
Garside

(10) Patent No.: US 10,258,253 B2
(45) Date of Patent: Apr. 16, 2019

(54) CRYOGENIC COOLING APPARATUS AND METHOD SUCH AS FOR MAGNETIC RESONANCE IMAGING SYSTEMS

(71) Applicant: Oxford Instruments Nanotechnology Tools Limited, Oxon (GB)

(72) Inventor: John Garside, Warrington (GB)

(73) Assignee: Oxford Instruments Nanotechnology Tools Limited, Oxon (GB)

( * ) Notice: Subject to any disclaimer, the term of this patent is extended or adjusted under 35 U.S.C. 154(b) by 1009 days.

(21) Appl. No.: 14/415,519

(22) PCT Filed: Apr. 19, 2013

(86) PCT No.: PCT/GB2013/051000
§ 371 (c)(1),
(2) Date: Jan. 16, 2015

(87) PCT Pub. No.: WO2014/013217
PCT Pub. Date: Jan. 23, 2014

(65) Prior Publication Data
US 2015/0196221 A1    Jul. 16, 2015

(30) Foreign Application Priority Data
Jul. 19, 2012 (GB) .................................. 1212800.5

(51) Int. Cl.
*F25B 9/00* (2006.01)
*F25B 9/14* (2006.01)
(Continued)

(52) U.S. Cl.
CPC ............... *A61B 5/055* (2013.01); *F25B 9/14* (2013.01); *F25B 9/145* (2013.01); *F25B 49/022* (2013.01); *F25D 19/006* (2013.01)

(58) Field of Classification Search
CPC ...... F25B 9/00; F25B 9/10; F25B 9/14; F25B 9/145; F25B 49/022; F25B 2600/02;
(Continued)

(56) References Cited

U.S. PATENT DOCUMENTS 4,366,680 A * 1/1983 Lovelace .................. F25B 9/02
62/46.1
5,842,348 A * 12/1998 Kaneko ................. F25D 19/006
335/216
(Continued)

FOREIGN PATENT DOCUMENTS

DE     3943640 C2 * 2/1996 .............. F04B 37/08
EP     0999423 A1    5/2000
(Continued)

*Primary Examiner* — Frantz Jules
*Assistant Examiner* — Erik Mendoza-Wilkenfe
(74) *Attorney, Agent, or Firm* — Blank Rome LLP

(57) ABSTRACT

A cryogenic cooling apparatus comprises a supply gas line and a return gas line adapted to be coupled to a compressor. A coupling element is positioned in gaseous communication with the supply and return gas lines, the coupling element being adapted in use to supply gas to a mechanical refrigerator so that the pressure of said supplied gas is modulated by the coupling element in a cyclical manner. A sensing system is used to monitor the operational state of the mechanical refrigerator and a control system modulates the frequency of the cyclical gas pressure supplied by the coupling element in accordance with the monitored operational state. The mechanical refrigerator has a first cooled stage and a second cooled stage, the second cooled stage being adapted to be coupled thermally with target apparatus to be cooled. A selectively coupleable thermal link is provided for thermally coupling the first cooled stage of the mechanical refrigerator to the second cooled stage in dependence upon the operational state of the mechanical refrigerator. A method of use of the apparatus is also disclosed. The apparatus and method have particular application in a Magnetic Resonance Imaging system.

48 Claims, 12 Drawing Sheets

(51) Int. Cl.
*F04B 37/08* (2006.01)
*B01D 8/00* (2006.01)
*A61B 5/05* (2006.01)
*F25D 19/00* (2006.01)
*A61B 5/055* (2006.01)
*F25B 49/02* (2006.01)

(58) Field of Classification Search
CPC ......... F25B 2600/25; F25B 2600/0253; B01D 8/00; F04B 37/08; F04B 37/085; A61B 5/055; F25D 19/006
See application file for complete search history.

(56) References Cited

U.S. PATENT DOCUMENTS

2009/0293505 A1 12/2009 Wang
2012/0067065 A1* 3/2012 Ando ................... F04B 37/08
 62/55.5
2013/0023418 A1* 1/2013 Ackermann ............ F25B 9/10
 505/162

FOREIGN PATENT DOCUMENTS

| GB | 2301174 A | 11/1996 |
|----|-----------|---------|
| JP | H08232839 A | 9/1996 |
| JP | 09-166365 | 6/1997 |
| JP | H1174572 A | 3/1999 |

* cited by examiner

CRYOGENIC COOLING APPARATUS AND METHOD SUCH AS FOR MAGNETIC RESONANCE IMAGING SYSTEMS

This application is the U.S. national phase of International Application No. PCT/GB2013/051000, filed Apr. 19, 2013, which claims the benefit of United Kingdom Patent Application No. GB1212800.5, filed Jul. 19, 2012, the entire contents of which are hereby incorporated by reference.

FIELD OF THE INVENTION

The present invention relates to an apparatus and method for controlling a cryogenic cooling system, particularly one in which certain types of gas compressor are used to drive mechanical refrigerators. The invention finds particular advantage in the cooling system of a Magnetic Resonance Imaging (MRI) system.

BACKGROUND TO THE INVENTION

Low temperature properties such as superconductivity and superfluidity are now widely used in a range of different applications including Magnetic Resonance Imaging (MRI), superconducting magnets, sensors and in fundamental research. Historically, the evaporation of cryogenic liquids such as nitrogen or helium has been used as a cooling mechanism in order to reach the low temperatures required for such applications. Cryogenic liquids have associated disadvantages in that they are often "consumable" due to leaks within associated apparatus such as "in situ" liquefiers or storage vessels. Furthermore such apparatus for storing or otherwise handling cryogenic liquids is often bulky and requires special handling procedures. Such apparatus and procedures are somewhat incompatible with patient care environments.

More recently, closed cycle refrigerators (CCR) have been used to replace cryogenic liquids in providing an alternative refrigeration mechanism. In contrast with the evaporation of cryogenic liquids, CCRs do not rely upon a phase change within the coolant. Indeed, CCRs operate upon a principle of using the cooling which is associated with the work of compression and expansion of a working gas coolant. Accordingly, the use of CCRs is of particular interest for cooling apparatus for medical applications, such as MRI. The term "mechanical refrigerators" is used herein to describe such apparatus although those of ordinary skill in the art will appreciate that the term "cryocooler" is synonymous with this term.

Mechanical refrigerators use a working gas such as helium to provide cooling at relatively modest cooling powers, to a temperature of 2 to 20 Kelvin. Mechanical refrigerators are extremely advantageous since they are closed systems with few moving parts and are essentially lossless with regard to the working gas. For these reasons, they are attractive both technologically and commercially and there is an on-going desire to improve the performance of such mechanical refrigerators.

Despite advances which have been made to date in the technology associated with mechanical refrigerators, the thermodynamic coefficient of performance (COP) and the associated cooling efficiency of such mechanical refrigerators are still rather unsatisfactory. As an example, an input electrical power of up to around 8 kiloWatts is needed in order to provide a cooling power of around 1 Watt at the liquid helium temperature of 4.2 Kelvin. There are numerous applications, such as the cooling of superconducting magnets (for use in MRI for example) or the cooling of relatively high thermal masses, where the cooling time required to cool from room temperature to the low temperature regime is an important parameter. It will be appreciated that it is desirable to reduce this cooling time to as short a period as possible. This is particularly desirable in MRI applications in patient care environments where long cooling down periods are unacceptable.

One technique developed by the present applicant to reduce the cooling time involves the introduction of a heat pipe between two cooled stages of the mechanical refrigerator. This technique is described fully within our United Kingdom patent application number 1119846.2, the contents of which are incorporated herein by reference.

The present applicant has continued developing techniques for improving upon the cooling time in such systems and it is in this context that the present invention finds application and provides new advantages.

SUMMARY OF THE INVENTION

In accordance with a first aspect of the present invention there is provided a cryogenic cooling apparatus comprising:
 a supply gas line and a return gas line adapted to be coupled to a compressor when in use;
 a coupling element in gaseous communication with the supply and return gas lines, the coupling element being adapted in use to supply gas to a mechanical refrigerator, the pressure of said supplied gas being modulated by the coupling element in a cyclical manner;
 a sensing system adapted to monitor the operational state of the mechanical refrigerator when in use; and,
 a control system adapted to modulate the frequency of the cyclical gas pressure supplied by the coupling element in accordance with the monitored operational state;
 wherein the mechanical refrigerator comprises:
 a first cooled stage and a second cooled stage, the second cooled stage being adapted to be coupled thermally with target apparatus to be cooled; and,
 a selectively coupleable thermal link for thermally coupling the first cooled stage of the mechanical refrigerator to the second cooled stage in dependence upon the operational state of the mechanical refrigerator.

This invention combines the benefits of a selectively coupleable thermal link and operational state dependent variable timing in the mechanical refrigerator to provide both increased cooling power at higher temperatures and increased thermal communication between the first and subsequent stages at higher temperatures, both effects being controllable to turn off at lower temperatures. By combining each of these technologies in a single apparatus, the cool down time of cryogenic equipment could theoretically be reduced by as much as 50% to 75%. The invention is applicable to a number of different types of mechanical refrigerators including pulse tube refrigerators, Gifford-McMahon refrigerators and Stirling coolers. The typical operational base temperature of the first cooled stage is between 20 and 80 Kelvin, whilst that of the second cooled stage is below 10 Kelvin.

The selectively coupleable thermal link may take a number of forms, including a heat pipe, a heat switch such as a gas gap heat switch, or a mechanical link. The thermal link is selectively coupleable in the sense that the thermal link may be made or broken in response to the operational state of the apparatus. The operation of the link may be automatic in the sense of being under the control of the control system. In some forms it may be automatic in an autonomous sense, in that it is directly responsive to the operational state and requires no specific exterior control. It is contemplated that more than one such thermal link may be provided, for example to operate within different temperature regimes between common first and second cooled stages, or to operate between different pairs of cooled stages in the case of the use of a mechanical refrigerator having a number of stages in excess of two.

This "short-circuiting" in a thermal sense between the first stage and the cooled member is counter-intuitive although, as we have realised, that this can lead to a significant practical advantage. The cooling power of mechanical refrigerators is usually acceptable in their steady state, that is when the lowest temperature stage is at its nominal base temperature and the target apparatus being cooled is also at approximately that temperature. In this case the cooling power of the mechanical refrigerator needs only to be able to deal with the heat load caused by either the operation of the target apparatus or from the external environment.

The limitations of mechanical refrigerators are therefore temporary and manifest themselves most strongly during the cool-down period when the target apparatus is not yet at its nominal base temperature and the mechanical refrigerator is not yet operating in a steady state. It is in this cooling regime that the invention finds its greatest advantage and application. In particular, we have realised that a thermal link can be used to provide the cooling power from the first stage (which is much higher than that of the second stage) to the second stage and therefore to the target apparatus.

At high temperatures, typically above 70 Kelvin, the first stage of the mechanical refrigerator is noticeably more powerful than the second stage in terms of cooling power. However, since most of the experimental payload is thermally coupled only to the second stage, the cooling power of the first stage is mostly wasted in known systems resulting in the second stage (and the target apparatus) cooling far more slowly than the first stage.

Thus, in addition to improving the cooling power by controlling the operational frequency of the mechanical refrigerator, the invention enables the power of the first stage to assist in the cooling of the second stage.

The sensing system monitors the operational state of the mechanical refrigerator. Such an operational state is dependent upon the conditions within the mechanical refrigerator, these typically including pressure and temperature conditions. One or each of the temperature and pressure may be monitored and further beneficial data may be obtained by logging time dependent changes in such parameters. For example the sensing system may comprise a pressure sensing apparatus adapted to monitor the pressure in at least one of the supply and return gas lines. Hence the pressure in one or each of the supply or return gas lines, when connected to an operational compressor, can be used to provide feedback upon the operational status of the mechanical refrigerator which changes as such a refrigerator undergoes a cooling cycle.

With knowledge of how the pressure response of the mechanical refrigerator provides information about the stage of the cooling cycle (for example the temperature achieved within a particular stage of the mechanical refrigerator), information regarding the pressure can be used to modulate the frequency at which the cyclical gas pressure is applied. Since the "optimum" frequency changes as the mechanical refrigerator cools, it is possible to modulate the frequency so as to approach or obtain the optimum frequency (as a function of temperature) during the cooling cycle. More than one "optimum" frequency may be existent, depending in particular upon whether the primary objective is to provide maximum cooling power to the first or second cooled stages.

The pressure sensing apparatus may comprise a pressure sensor such as a pressure transducer for monitoring the pressure in at least one of the supply or returning gas lines. The invention can be achieved readily with use of a single sensor in one of these lines although one or more sensors in either or each line are contemplated. It is desirable that the minimum apparatus required for the application in question is provided in the pressure sensing apparatus so as to provide sufficient information regarding the state of the mechanical refrigerator in order to provide sufficient control over the gas supply frequency.

One advantage of using the monitored pressure within one of the gas lines to provide the information upon the cooling cycle is that this avoids the need for direct sensing of the environment within the cooled part or parts of the mechanical refrigerator. As will be understood, in this case the sensor is not located within the cooled part of the mechanical refrigerator.

As an alternative or additional method of monitoring the operational state, the apparatus may further comprise temperature sensing apparatus for monitoring the temperature within a cooled region of the mechanical refrigerator. Here, as for the pressure monitoring, the control system is adapted to control the frequency of the cyclical gas pressure in accordance with the temperature monitored by the temperature sensing apparatus (or in accordance with each of the temperature and pressure where such information is monitored). Although in principle the temperature may be monitored at many different locations within the mechanical refrigerator, preferably the sensing system comprises temperature sensing apparatus adapted to monitor the temperature in one or more of the first cooled stage, the second cooled stage or the thermal link. One or more thermocouples may be used for this purpose.

The operational frequency of the mechanical refrigerator is effected by the coupling element. The invention is not limited by the particular coupling element used to connect the mechanical refrigerator to the compressor. Such a coupling element may typically comprise one or more valves, these typically being cyclical valves. Various types of valves may be used although in the present application a rotary valve is particularly advantageous. The coupling element is typically driven by a motor such as a stepper motor, a 3-phase asynchronous electric motor or linear DC motor driven by a variable DC power supply. The speed of such a motor drive is typically controlled by the control system to deliver the required operational frequency.

With further reference to the thermal link, a heat pipe is one example of a thermal link. Typically in such a case the heat pipe has a first part coupled thermally to the first stage of the mechanical refrigerator and a second part coupled thermally to the second stage of the mechanical refrigerator, the heat pipe being adapted to contain a condensable gaseous coolant when in use and the apparatus being adapted in use to be operated in a first cooling mode in which the temperature of the cooled member causes the coolant within the second part of the heat pipe to be gaseous and the temperature of the first stage causes the coolant in the first part to condense, whereby the cooled member is cooled by the movement of the condensed liquid from the first part to the second part of the heat pipe.

The heat pipe is typically a gas heat pipe that is temperature-driven, as discussed herein, or of any other type. The heat pipe therefore contains, when in use, a gaseous coolant which is capable of being condensed into coolant liquid in the apparatus. The generation of the liquid condensate provides a vehicle for the cooling power of the first stage to be delivered to the second stage of the mechanical refrigerator. This will almost always be a "gravity-driven" process or could use alternative processes such as the expansion of vaporised coolant to drive the fluid flow.

Whilst the apparatus is adapted to be operated in a first cooling mode within which the invention finds particular advantage, the apparatus is preferably further adapted in use to be operated in a second cooling mode in which the temperature of the first stage in the mechanical refrigerator causes the freezing of the coolant and causes the temperature of the second stage to become lower than the temperature of the first stage. Thus, upon cooling from ambient temperature for example, the apparatus will enter the first cooling mode before entering the second cooling mode. It is therefore preferable to use a coolant which is capable of adopting gaseous, liquid and solid states at temperatures obtainable by the respective stages of the mechanical refrigerator.

It will be appreciated that the choice of the type of coolant and indeed the pressure at which it is supplied to the heat pipe is application specific. One difficulty encountered with the use of mechanical refrigerators is that the actual temperatures attained by the various stages of the mechanical refrigerators when not in a steady state are difficult to control. This causes a problem since the heat pipe will only function effectively if the first part can be cooled to a temperature which causes condensation of the gaseous coolant whereas that of the second part causes evaporation.

Upon operating the mechanical refrigerator, the temperature of the first stage may soon fall below the temperature at which the coolant may remain as a liquid and therefore it may solidify which thereafter prevents the heat pipe from operating. In order to prolong such a regime and therefore to maintain the apparatus within the first cooling mode as long as desired, preferably the apparatus control system is further adapted to control the environment in the first part of the heat pipe when the apparatus is in the first cooling mode so as to ensure that the gaseous coolant is able to condense but not freeze.

The control system may achieve this by modulating the frequency of the cyclical gas pressure in order to control the environment in the heat pipe. In particular, this may involve holding the operational frequency at a constant value when the heat pipe (or parts thereof) is within a specific temperature range, or otherwise changing the operational frequency, such as according to a function of temperature within the range. As an alternative or additional approach the apparatus may comprise a heater in thermal communication with the heat pipe for use in controlling the environment in the heat pipe.

The heat pipe may comprise a single coolant gas or mixture of gases sealed within the heat pipe. Typically the gas may comprise one or more gases selected from the group of: Nitrogen, Oxygen, Xenon, Argon, Krypton, Carbon Dioxide, Hydrogen.

The apparatus may also further comprise an external volume which is placed in fluid communication with the interior of the heat pipe. Such a volume may take the form of a reservoir or storage tank and may be used not only to supply the heat pipe coolant to the heat pipe initially but also to control the pressure of the gas within the heat pipe during the various stages of operation of the apparatus. Thus such an external volume may be used by the control system as part of a pressure control function.

It will be appreciated that the interior of the heat pipe typically comprises an internal volume for containing the coolant and which contains the first and second parts in fluid communication with one another. Thus the geometry of the volume may be very simple; indeed it may take the form of a simple cylindrical volume. The first and second parts are typically corresponding first and second ends or end regions of the heat pipe, particularly in the case of a generally cylindrical volume. Regardless of the exact geometry, the first and second parts are typically thermally isolated from each other. It should also be noted that the heat pipe components may contain, be attached to or be incorporated within other components of the mechanical refrigerator. For example they may contain part of the piping used to form the second cooled stage in particular.

The description above discusses the provision of a mechanical refrigerator having first and second stages. It is however known for some mechanical refrigerators to include three stages and higher numbers are also possible. It will be appreciated that the invention may be used with such mechanical refrigerators having three or more stages and, in principle, the thermal link may be used to provide cooling between any selected pair of such stages. Indeed, two instances of the thermal link could be used to cool between a first stage and an intermediate stage (using a first instance) and between the intermediate stage and the second stage (using a second instance). This might be the case for example when an intermediate stage is used for cooling other apparatus (such as radiation shields). It is also contemplated that a thermal link might be used to provide cooling power between a first and third stage, and a second between a second and third stage. In each case the operational frequency of the apparatus would be modulated according to the particular desired cooling to be achieved.

The invention is not limited to the use of any particular kind of target apparatus although great advantage is provided where the thermal mass of the target apparatus is high. The target apparatus includes experimental apparatus or may for example be the still or mixing chamber of a dilution refrigerator for very low temperature experiments. The thermal connection between the mechanical refrigerator and the target apparatus may be rigid such as by physical clamping, or via a flexible coupling such as an anti-vibration coupling. An example of such an anti-vibration coupling would be braids of high thermal conductivity copper, these being used to maximise the cooling effect whilst keeping the transmission of vibrations between the target apparatus and the lowest temperature stage to a minimum.

It is known that vibrations are a particular problem in apparatus cooled using mechanical refrigerators and therefore a further benefit is provided when the heat pipe comprises walls within which are positioned bellows, these having a vibration-dampening effect.

It will be recalled that the primary advantage of the invention is gained during the cooling of the apparatus. In the case of particularly sensitive target apparatus the provision of the thermal link could potentially reduce its operational effectiveness during the steady state operation of the mechanical refrigerator. This might occur due to the thermal link providing a weak path for heat to travel between the stages of the mechanical refrigerator. It is therefore preferred in the case of the heat pipe to provide an anti-radiation member which is operative to reduce the passage of electromagnetic radiation between the first and second parts of the heat pipe. The anti-radiation member is arranged in a manner which nevertheless allows the heat pipe to operate and therefore allows passage of liquid from one side of the member to the opposing side. Thus the coolant may pass around the edge of the member or through one or more small apertures therein. The anti-radiation member may alternatively be one or more bends formed in the heat pipe so as to ensure there is no direct line of sight between the two ends of the heat pipe.

An alternative example of a thermal link is a gas gap heat switch. Typically such a gas gap heat switch comprises a first thermally conductive member in thermal communication with the first cooled stage, a second thermally conductive member in thermal communication with the second cooled stage, wherein the said first and second conductive members being separated by a gap region to which a heat switch gas may be selectively provided; and, a gas source for selectively providing the heat switch gas to the gap region at a first pressure so as to cause thermal communication between the first and second members through the said heat switch gas, and at a second pressure, lower than the first pressure, so as to thermally isolate the first and second members from each other.

Advantageously the gas source may comprise an adsorbent material exhibiting temperature dependent adsorption behaviour with respect to the heat switch gas. Charcoal is one example of a number of suitable materials for this purpose. Preferably the said first and second members are contained within a gas-tight chamber which extends between the first and second cooled stages. This provides a containment vessel for the heat switch gas and aids in providing some further mechanical stability between the first and second stages. When the gas source is in the form of an adsorbent material it may be provided adjacent to the second thermally conductive member, preferably within the gas-tight chamber. This provides for a compact self-contained operation.

However, since the adsorbent material behaviour may then be dependent upon the temperature of the second cooled stage, another advantageous arrangement is to place the adsorbent material in a separate vessel which allows the temperature of the material to be controlled independently of the second cooled stage. Preferably, the gas source is adapted to be controlled by the control system, for example by the use of a heater to control the adsorbent material temperature in conjunction with cooling power provided by the mechanical refrigerator, through a weak thermal coupling for example.

As a further example, the thermal link may take the form of a mechanical link. Various mechanical links are envisaged, these typically being operational by using the thermal coefficient of expansion of a material to cause thermal contact or thermal isolation between two members due to resultant relative movement between parts of such members. A bimetallic strip arrangement is an example of one such link. Preferably however, the mechanical link comprises a first thermally conductive member in thermal communication with the first cooled stage, a second thermally conductive member in thermal communication with the second cooled stage, wherein at least one of the said first and second conductive members comprises a thermally conductive spring element arranged to expand during cooling of the apparatus so as to conduct heat between the first and second members when the said first and second members are within a predetermined temperature range. Notably one of the members in this case may be a surface of one of the cooled stages. The provision of the conductive spring element is not essential in all applications although it is advantageous in that it may allow the operation of the link over a larger temperature range than would otherwise be possible in the absence of such a spring. The spring itself may be formed from a high thermal conductivity material or, where such materials do not exhibit a sufficient coefficient of thermal expansion, a layer of high thermal conductivity material may be coated upon a second material with a higher coefficient of thermal expansion.

The thermal links may be positioned in a number of different arrangements. For example the thermal link may be positioned around or within a pulse tube which leads to the second cooled stage, and between the first and second cooled stages. It may be positioned around or within the part of a regenerator tube between the first and second cooled stages. In the case of a Gifford-McMahon (GM) cryocooler it may be located around a second cooled stage tube of the GM cryocooler. Regardless of the mechanical refrigerator utilised, a number of thermal links may be provided, either of different or similar types.

In accordance with a second aspect of the invention there is provided a cryogenic cooling system comprising:
  apparatus according to the first aspect of the invention; and,
  a compressor in gaseous communication with the supply and return gas lines.

A number of different types of compressor may be used depending upon the application, these including a scroll compressor, rotary screw compressor, rotary vane compressor, rotary lube compressor or a diaphragm compressor. Each of these compressors shares the common features of supply and return lines for the compressor gas. The supply line may be thought of as a relatively high pressure line and the return line may be thought of as a relatively low pressure line for use with the invention.

The cryogenic cooling apparatus and cryogenic cooling system as discussed above in accordance with the invention find particularly advantageous application and use in the field of magnetic resonance, and in particular, magnetic resonance imaging.

In accordance with a third aspect of the present invention there is provided a magnetic resonance system comprising: a magnet system comprising a number of magnets for generating a magnetic field which is suitable for obtaining magnetic resonance signals from a target region; a radio frequency system for obtaining radio frequency signals from the target region; a control system for controlling the magnetic fields experienced within different parts of the target region in accordance with the magnet system and radio frequency system; a processing system for forming an image from the radio frequency signals; and, a cooling system adapted in use to cool one or more of the magnet system or radio frequency systems using a cryogenic cooling apparatus according to the first aspect.

The magnet system typically includes superconductive magnets and wherein the cryogenic cooling system further comprises a heat transfer medium which is arranged to act as a heat sink for the superconductive magnets and wherein the pulse tube refrigerator is operative to extract heat from the heat transfer medium when in use. Such a medium may take the form of a liquid coolant, a gaseous coolant or a solid high thermal conductivity material such as high purity copper.

In accordance with a fourth aspect of the present invention there is provided a method of controlling an apparatus in accordance with the first aspect of the invention, the method comprising:
  monitoring the operational state of the mechanical refrigerator using the sensing system; and,
  modulating the frequency of the cyclical gas pressure supplied by the coupling element in accordance with the monitored state.

As will be appreciated following the discussion of the first aspect of the invention, preferably the step of monitoring comprises monitoring one or each of: the pressure in at least one of the supply and return gas lines, or the temperature within the mechanical refrigerator. With regard to the control of the frequency of the mechanical refrigerator, typically the coupling element is moveable in a rotational manner and wherein the frequency is effected by moving the coupling element at a corresponding rotational speed. In practice, the provision of a desired frequency may be effected by a desired motor current or speed in situations where the coupling element is driven by a motor.

Typically, the frequency of modulation of the cyclical gas pressure is arranged to be in accordance with a predetermined relationship. Such a relationship may include a function such as a linear or polynomial function, or other mathematical relationship. It may also be provided by a stepwise relationship between the pressure and the frequency provided. It may also be effected by the use of look-up tables rather than direct calculation. In each case the application of the relationship during the method may be achieved by a looped staged process, such as embodied in an algorithm executed by suitable software. The pressure or temperature data indicative of the operational state may be sampled and processed such that the appropriate frequency may be evaluated for each loop of the algorithm, this allowing an immediate "real-time" response to changes in pressure.

Within at least some temperature regimes it is preferred that the frequency is modulated so as to maintain the monitored pressure within a predetermined pressure range. Such a range may be narrow such as a small percentage of the expected pressure change during the operation of the mechanical refrigerator. It may tend towards a single pressure value in practice. The magnitude of the range may be dependent upon a number of parameters of the apparatus, including the degree of control which can be achieved over the pressure as the mechanical refrigerator cools. The predetermined pressure range is typically set in accordance with a maximum operational pressure of the apparatus. Such a maximum pressure may be determined by the mechanical refrigerator or the compressor for example. The predetermined pressure range may be set as close to the maximum pressure as is practical within safety parameters. This condition may be overridden in situations where the thermal link is operational or when low temperatures are achieved within the mechanical refrigerator.

The operational frequency range is also typically controlled so as to provide boundary conditions to the predetermined relationship. For example, if, in accordance with the predetermined relationship, the frequency would, according to the relationship, be below a minimum threshold frequency then the frequency is set to the minimum threshold frequency. This typically occurs in practice where it is found that the optimum frequency for operating the mechanical refrigerator at the base temperature is achieved, according to the relationship, when the mechanical refrigerator is above the base temperature. As an example this may be achieved at a temperature of around 60K even when the base temperature is around 4K.

Similarly, if, in accordance with the predetermined relationship, the frequency would, according to the relationship, be above a maximum threshold frequency then the frequency is set to the maximum threshold frequency.

Preferably the operational frequencies used in the method are in the range 1 to 5 Hz. The operational pressures are typically in the range 1 to 40 MPa.

The invention is not limited to any particular type of coolant gas although it is preferred that the coolant gas is helium. Helium is the preferred coolant for cryogenic applications in which very low temperatures of around 2 to 4 Kelvin are obtainable by the mechanical refrigerator.

In cases where the thermal link comprises a heat pipe the method typically comprises:
i) providing a predetermined quantity of coolant to the interior of the heat pipe;
ii) causing the second cooled stage to adopt a temperature sufficient to ensure the coolant within the second part of the heat pipe is in the gaseous phase;
iii) operating the mechanical refrigerator to cause the first stage of the mechanical refrigerator to adopt a temperature which causes the coolant within the first part of the heat pipe to condense; and,
iv) cooling the second cooled stage by causing the movement of the condensed coolant from the first part to the second part of the heat pipe.

Furthermore, in this case preferably the method further comprises:
v) operating the mechanical refrigerator after step (iv) to cause the first stage of the mechanical refrigerator to adopt a temperature which causes the coolant within the first part of the heat pipe to freeze; and,
vi) further operating the mechanical refrigerator such that the second stage cools to an operational temperature lower than that of the first stage for using in cooling the target apparatus.

In cases where the thermal link comprises a gas gap heat switch the method preferably comprises using the control system to operate the gas source so as to apply or remove the working gas from the gap region. In order to achieve this, the said operation of the gas source may comprise operating a heater in thermal communication with the gas source.

Hence the operation of the thermal link may be arranged to be independent of the frequency control. However, in order to provide further enhanced cooling performance, the operational frequency of the mechanical refrigerator may be modulated in accordance with the monitored operation of the thermal link. Thus the method may further comprise using the sensing system to monitor the temperature in one or more of the first cooled stage, the second cooled stage or the thermal link and maintaining the operation of the thermal link by either reducing the cooling power applied to the first cooled stage or by locally heating one or more of: the thermal link or the first cooled stage. Typically, when the said maintaining of the operation of the thermal link is provided by reducing the cooling power applied to the first stage, the method comprises the system controller modifying the frequency of the cyclical gas pressure supplied by the coupling element. The modified frequency may be a constant frequency or a frequency dependent upon the operational temperature of the thermal link. In either case the maintaining or prolonging of the operation of the thermal link may be dependent upon the monitored temperature being within a predetermined temperature range. It is noted here that the sensing system may monitor the temperature directly by the use of thermocouples or other temperature sensing apparatus, or may monitor the temperature by the monitoring of another indirect parameter such as one or more pressures within the mechanical refrigerator, such parameters having a predetermined relationship with respect to the temperature.

Whilst the primary utility of the method is during the cooling cycle of a mechanical refrigerator, it will be appreciated that the process may usually be applied whilst heating up an operational mechanical refrigerator from the base temperature.

In accordance with a fifth aspect of the invention there is provided a method of controlling a magnetic resonance system in accordance with the third aspect, the method comprising: controlling the cryogenic cooling apparatus to cool one or more of the magnet system or radio frequency systems to a working temperature; providing at least one radio frequency signal in order to obtain radio frequency signals from the target region; controlling the magnetic fields produced by the magnet system in accordance with a desired imaging location of the target region; and, processing the obtained radio frequency signals in order to form an image of the desired imaging location of the target region.

When the magnet system comprises superconducting magnets, the working temperature is below the critical temperature of the magnets such that they are in the superconducting regime (a typical working temperature is 4.2K). As is well known, the magnetic fields are controlled such that the final image comprises a series of "slices" through the target region (a patient for example), the spatial location of the slices being determined by the magnetic fields produced by the magnet system.

BRIEF DESCRIPTION OF THE DRAWINGS

Some examples of a cryogenic cooling apparatus and method are now described with reference to the accompanying drawings, in which.

DESCRIPTION OF PREFERRED EXAMPLES

Figure 10:
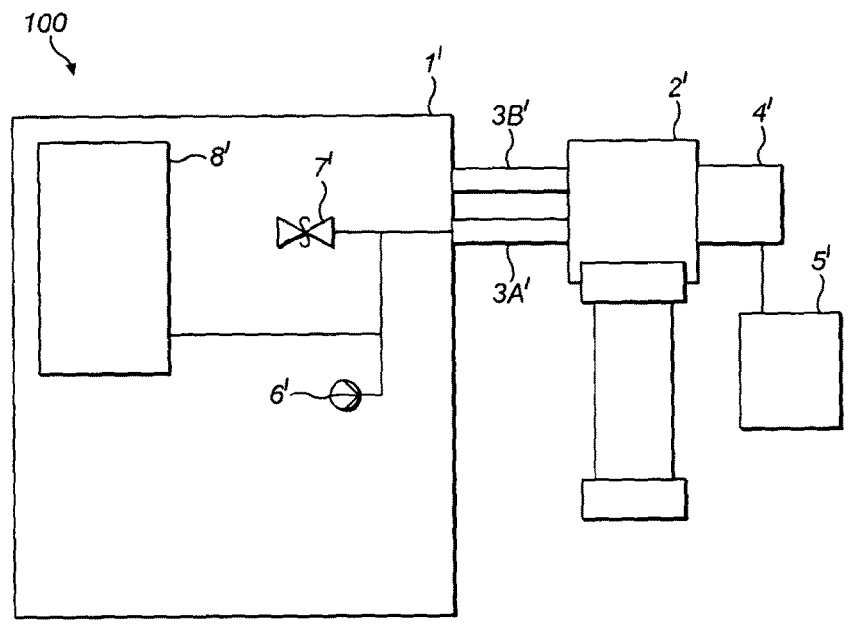
FIG. 10 shows a schematic overview of the main components of a known cooling apparatus.

In order to provide a full understanding of the invention, we firstly describe a known closed cycle refrigerator (CCR) system in accordance with FIG. 10. The system described uses a mechanical refrigerator in the form of a pulse tube refrigerator (PTR). However, as will become clearer from the further description later, the system according to the invention may also be used with other coolers such as a Gifford-McMahon (GM) cooler.

The system 100' comprises a scroll compressor 1' and a pulse tube refrigerator (PTR) 2'. Two gas lines 3A' and 3B' connect the scroll compressor 1' to the pulse tube refrigerator 2'. The gas lines 3A' and 3B' are essentially gas pipes which are capable of withstanding a high pressure. The gas line 3A' is a supply line which contains a coolant gas at a high pressure when in use. The line 3B' is a return line in the form of a low pressure line. Notably each of the high and low pressures is significantly above atmospheric pressure, for example 23-28 atmospheres and 3 to 10 atmospheres respectively. A coupling element, in this case in the form of a rotary valve 4', is illustrated as an integral part of the PTR 2'. The rotary valve 4' is driven by a system controller 5' and the operational speed of the motor is fixed to ensure a constant rotational frequency of the rotary valve given by a frequency denoted "Foptimum". This frequency is designed to be the optimum frequency for use of the PTR once at its "cold" or steady-state operational temperature.

Optionally, a pressure sensor 6' may be present within the compressor so as to detect an abnormal pressure within the high pressure line 3A'. The scroll compressor 1' is also provided with a bypass system 7' which is caused to operate when a critical value of pressure within the high pressure line is detected. In known systems, the critical pressure within the high pressure line 3A' is always reached at the beginning of a cool-down process and remains for a relatively long period of the cool-down process. Depending on the type of mechanical refrigerator, such a period can be at least one third and up to one half of the full cooling time required to reach the low temperature regime.

Whilst a critical value of the pressure exists, the bypass 7' remains open and allows coolant gas to pass between the high pressure supply line and the lower pressure return line. In this case the coolant gas is helium and the operation of the bypass 7' ensures that no helium is lost to the external atmosphere. This is important since helium is an expensive gas.

The above described example represents a standard prior art CCR system in which a mechanical refrigerator (cryocooler) is driven by a compressor. The known mechanical refrigerator may take various forms including GM coolers, Stirling coolers, pulse tube refrigerators, cold heads and cryopumps. In each of these types of CCR a rotary valve or other coupling element regulates the mass flow of the coolant gas transferred between the compressor and the mechanical refrigerator. In order to maximise the cooling power available at low temperatures, the mechanical refrigerator is designed such that, when in the steady-state or cold condition, the PTR (or equivalent) helium mass flow matches the compressor's optimum working point. Therefore in each mechanical refrigerator an optimum frequency value Foptimum for the rotary valve or other type of coupling element exists in order to maximum the cooling power.

It is notable however that an important physical property of helium, and indeed of other gases, is that the density of the gas increases as the temperature decreases. In cryogenic systems with mechanical refrigerators, the temperature difference between room temperature and the operational temperature is approximately 290 Kelvin which is a very significant temperature difference. At an operational temperature of around 2 to 4 Kelvin, the density of the helium gas coolant is significantly higher than that at room temperature. With an operational pressure of some atmospheres, the density value of the helium at 4K is more than 100 times higher than its equivalent density at room temperature (300K).

In the conventional CCR system described above, at the beginning of the cool down process, the mass flow of coolant gas delivered by the compressor cannot be fully transferred via the rotary valve to the PTR. This is because the operational frequency of the coupling is too low (a few Hertz). As a result, pressure may build upon the high pressure side of the compressor. Depending upon the initial filling pressure value of the system, a critical limit value may be exceeded. Typically a safety valve is set to operate below a critical value for this pressure and such a safety valve is positioned within the high pressure line. It is known to either vent the excess pressure to the external atmosphere or, as is shown in FIG. 10, to provide the safety valve in the form of a bypass 7' which effectively vents the helium to the low pressure side of the compressor.

The coolant gas pressures in each of the high pressure supply line 3A' and low pressure return line 3B' are provided by power from a compressor motor 8'. The bypass may therefore take the form of an over pressure valve and this is desirable in comparison with a valve which vents the helium to atmosphere since the helium is not lost from the system if a critical value of the pressure is reached. Nevertheless, during the initial cool down, the critical value is always reached at the beginning of the cool down procedure.

Later, as the low temperature steady-state regime is approached, the pressure reduces and the bypass closes. Once the low pressure has reduced to the operational pressure in the steady-state, the frequency of the rotary valve and the pressure which it controls (having a frequency of Foptimum) attain the optimum for the operational temperature.

Some examples of CCR systems according to the invention are now described.

Figure 1:
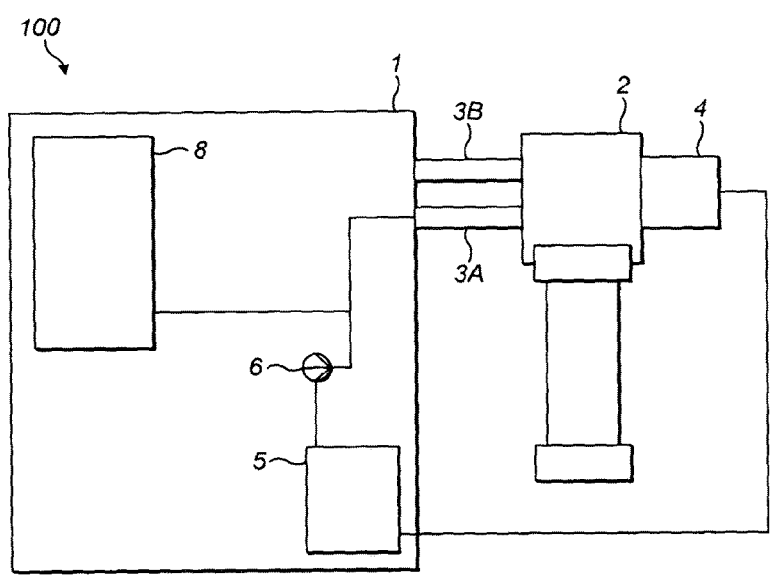
FIG. 1 shows a schematic overview of the main components of the cooling apparatus according to the examples.

We firstly discuss the apparatus generally with reference to FIG. 1 and how it compares to the prior art system described in association with FIG. 10. There are two main distinctions between the apparatus described above and that now described in the various examples according to the invention. Firstly, the example apparatus includes a system for monitoring the operational state, such as the cooling state, of the mechanical refrigerator, and the operational frequency of the mechanical refrigerator is controlled accordingly in dependence upon the monitored operational state. Secondly a selectively coupleable (engageable) thermal link is provided to connect at least two of the cooled stages thermally, thus allowing a faster cool down of the coldest stage, using the cooling power from the (or a) higher temperature stage.

In FIG. 1, apparatus having analogous features with those in FIG. 10 is provided with similar reference numerals, absent the ending "prime".

In FIG. 1, the CCR system according to the invention is illustrated at 100. A scroll compressor 1 is connected via high (3A) and low (3B) lines to a PTR 2, with similar operational pressure ranges in these lines as in FIG. 10. A coupling element in the form of a rotary valve 4 again controls the PTR 2. In this example the rotary valve 4 is operable at a variable frequency F. In this case, the modified system controller is a more general system controller 5 and receives a signal from the pressure transducer 6. This transducer is a pressure sensor which provides a monitoring signal which can be related to the pressure magnitude sensed by the transducer. The signal is provided to the system controller 5. The system controller 5 contains a processor and associated programmable memory. The processor samples the signals from the pressure transducer 6 and, using an appropriate algorithm or look-up table, converts these to a suitable control signal which is outputted to the rotary valve 4. This is illustrated in FIG. 1 by the lines linking the pressure transducer 6 to the system controller 5, and the system controller 5 to the rotary valve 4. The system controller 5 therefore provides a control mechanism for operating the CCR 100. It will be appreciated that the components shown in FIG. 1 are illustrated schematically and therefore other ordinary equipment which is not specifically shown such as safety valves, oil separators, filters, heat exchangers, sensors and so on, is nevertheless present.

The example apparatus as shown in FIG. 1 therefore has the same benefits as the apparatus in FIG. 10 during steady-state low temperature operation of the mechanical refrigerator in the form of the PTR 2. However, it also allows improved efficiency to be achieved during the cool down procedure. This is achieved by varying the rotary valve mechanism frequency so as to dynamically accommodate the helium mass flow exchange between the PTR 2 and the compressor 1. At high temperatures, such as those close to room temperature, the rotary valve 4 is operated with a corresponding frequency regime that is significantly higher than the optimum design frequency Foptimum which is associated with the PTR 2 at its steady-state low temperature. Due to the high frequency regime, the pressure within the high pressure side of the compressor is reduced in comparison with prior art systems and therefore the mechanical refrigerator is able to operate without losing efficiency at the initial high temperature. Later, when the PTR cools, the frequency regime can be reduced in order to approach and then obtain Foptimum as the steady-state temperature is reached.

The overall efficiency of the CCR 100 is therefore considerably improved in comparison with that of known systems such as 100' in FIG. 10. In this particular example, the frequency F is electronically controlled in accordance with a signal from the pressure transducer in accordance with an automatic feedback mechanism which is regulated by the system controller 5. It is notable that no temperature sensors and no more than one pressure transducer 6 are used in this particular example. The key parameter is the maximum pressure allowed in the system, because this is typically the design limitation of the compressor and this governs the possible cooling efficiency of the mechanical refrigerator.

Thus the efficiency of the PTR 2 is maximised. It will be appreciated that an algorithm to optimise the frequency F as a function of the pressure experienced may be derived by calculation or by experimental measurements. A further variable for consideration in deriving for such an algorithm (or equivalent) is a consideration to ensure that overall vibrations are reduced.

The practical benefit of the example apparatus is that the CCR system 100 reaches the low temperature regime more quickly than the equivalent CCR system 100' shown in FIG. 10. The available cooling power at high temperatures is also considerably enhanced such that, even without the thermal link to be described below, an overall improvement of the key parameters of the system by at least 35% is observable.

A considerable benefit can be derived by the careful control of the rotary valve frequency even in the absence of a thermal link. However, the applicants have found that the frequency control of the coupling element can be used advantageously with the application of a selectively coupleable thermal link between cooled stages of the mechanical refrigerator. In the present example, such a thermal link is provided with the use of a "heat pipe" which is positioned between the first and second stages of the PTR. Further details of the heat pipe are now described.

Figure 11:
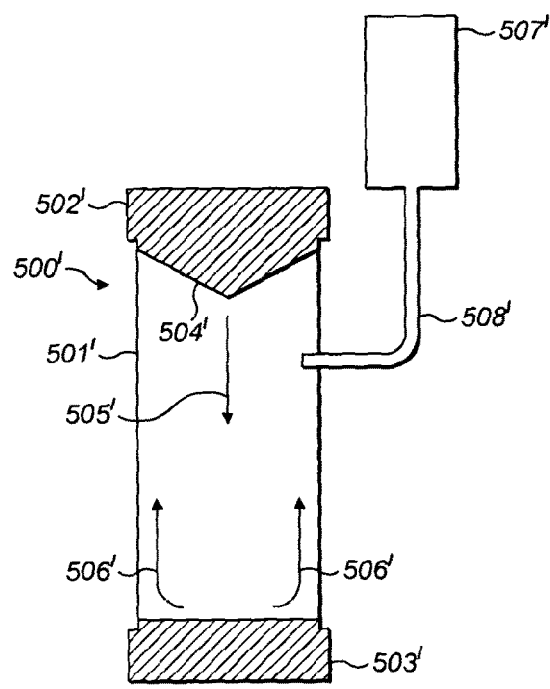
FIG. 11 shows the principle of operation of a known heat pipe.

FIG. 11 shows a schematic representation of a heat pipe 500', viewed partly in section from the side. The heat pipe can be thought of as a hollow cylinder having walls 501' extending along the axis of the cylinder. Each end of the heat pipe is sealed by respective end pieces. Since the heat pipe 500' normally adopts an approximately vertical orientation, the end pieces are defined by an upper end piece 502' and a lower end piece 503'. In FIG. 11 it will be noted that the upper end piece 502' has an internal surface which is formed in a frusto-conical manner (or as a hyperbolic cone) so as to provide a point 504' positioned approximately centrally within the cylinder (effectively along its axis). Typically the heat pipe walls 501' are formed from thin stainless steel. In addition, the end pieces 502', 503' are also typically formed from a high conductivity material such as high purity copper. Heat pipes such as that shown in FIG. 1 are known in the field of cryogenics and may be filled with a working fluid such as helium-4.

The principle of operation of a heat pipe is as follows. The interior of the heat pipe is sealed with a fixed amount of cryogen. The amount of cryogen used is calculated based upon the operational temperature and pressure at which the heat pipe is designed to operate.

The useful temperature range of a heat pipe is defined by the boiling point and the melting point of the cryogen inside it. A strong thermal link is achieved between the upper end piece 502' and the lower end piece 503' when the temperature of the upper end of the heat pipe is such that the gaseous cryogen within it can condense on the surface. Gravity then draws the liquid condensate down to the lowest point 504' of the upper end piece 502' from which it then drips directly to the lower end piece 503'. This is illustrated by the arrow 505'. The liquid arriving at the lower end of the heat pipe absorbs heat from the lower end which, if sufficient, causes the cryogen to evaporate and then pass upwards along the length of the heat pipe to the upper end piece 502'. The upward flow of gas is illustrated by the arrows 506'. Upon contacting the upper end piece 502', the cryogen gas again condenses and travels to the point 504' where it then falls again through the lower end as a liquid. Thus, a cycle is set up which is gravity-driven.

The continuous process of condensation on the upper surface and the evaporation on the lower surface produces a strong thermal link between the two respective ends of the heat pipe. This link is substantially weakened if the upper end of the heat pipe reaches the temperature which is too high for the condensation of the gas at a given operational pressure within the heat pipe. The thermal link therefore becomes significantly weakened since, although gaseous convection may occur, the enthalpy associated with the change of state between gas and liquid is no longer available. Conversely, if the temperature of the upper end of the heat pipe (or indeed of the lower end) is sufficiently low so as to cause solidification of the cryogen the thermal cycle effect ceases and the respective ends become thermally isolated from one another.

FIG. 11 also shows a room temperature expansion volume in the form of a reservoir 507'. This may be effected practically by a tank located external to the apparatus within the ambient environment. A tube 508' connects the interior of the reservoir 507' with that of the heat pipe 500'. Typically the tube is fitted with a valve (not shown). The reservoir 507' may be used to reduce the pressure within the heat pipe and whether or not such a reservoir is used somewhat depends upon the exact dimensions of the heat pipe and the pressure rating of its components.

Figure 2:
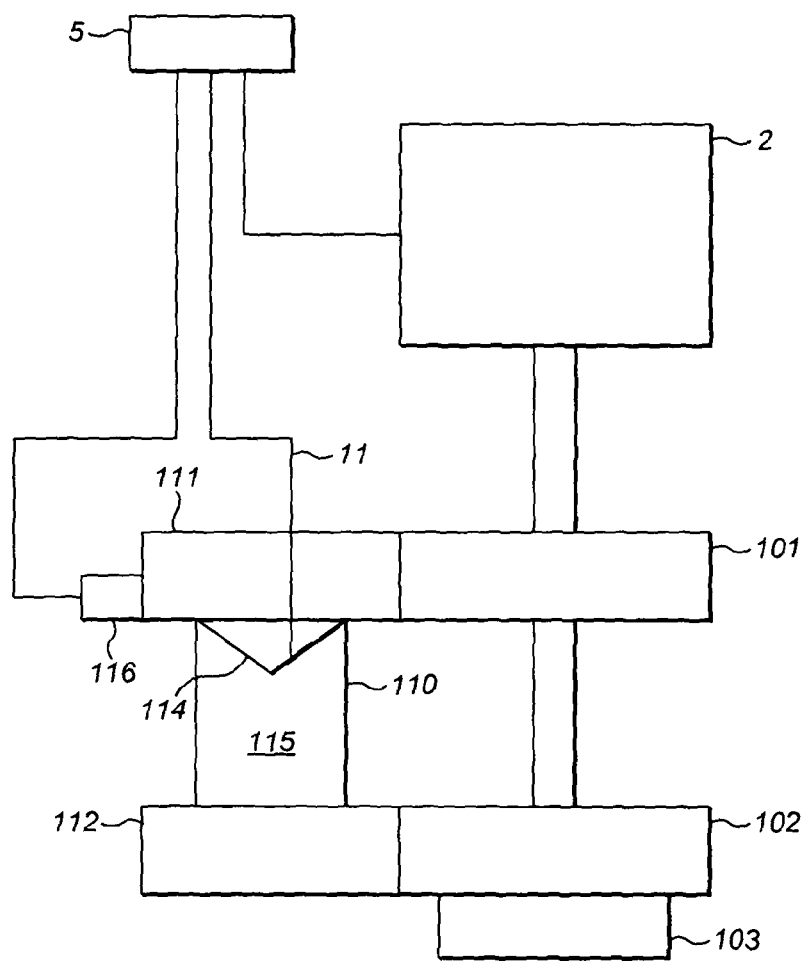
FIG. 2 shows details of a pulse tube refrigerator with thermal link in the form of a heat pipe according to a first example.

FIG. 2 shows a schematic arrangement of the thermal link apparatus according to the present example of the invention in relation to the mechanical refrigerator illustrated in FIG. 1. In the present case, the pulse tube refrigerator (PTR 2) is a two-stage PTR, having a first stage illustrated at 101 and a second stage at 102. As is known, during steady state operation, the second stage 102 of the PTR 2 attains a low temperature (such as a few Kelvin). This may be used to cool various types of target apparatus, including parts of a magnet system, experimental sensors or other apparatus for experimental use, or for example to pre-cool the still of a dilution refrigerator. Such a target apparatus 103 is illustrated as being attached directly to the second stage 102 of the PTR, this ensuring a good thermal link, thereby maximising the cooling power of the second stage of the PTR 2.

FIG. 2 also illustrates a heat pipe 110, positioned between the first and second stages 101, 102 of the PTR 2. The heat pipe 110 has an upper end 111 and a lower end 112, the upper end 111 being connected via a high thermal conductivity link to the first stage 111. Likewise the lower end 112 is also connected via a high conductivity link to the second stage 102 of the PTR 2. Such a link in each case may be provided via an intermediate member or may be simply by direct, high surface area, connection so as to maximise conductivity of heat across the interface between the respective end and stage. In this example an external volume in the form of a reservoir is not illustrated although it may well be present depending upon the specific application. The upper end 111 contains an internal frusto-conical surface 114. The inner volume within the heat pipe 110 is filled with Krypton gas as a coolant 115.

Although the heat pipe 110 is illustrated as being connected to one side of the respective stages 101, 102 of the PTR, it will be understood that this is a schematic representation. In practice, it may be advantageous to provide the heat pipe 110 within the "footprint", that is, the geometric envelope, of the PTR 2 since this allows for the retro-fitting of the apparatus to existing equipment as an upgrade to an existing PTR.

Although a PTR 2 is illustrated in FIG. 2, it will be appreciated that similar benefits of the invention may be achieved by the use of other mechanical-refrigerators with this particular example arrangement. A PTR is particularly advantageous since it does not contain moving parts within the low temperature region and therefore it is particularly useful for relatively low vibration operation at low temperatures.

The principle of operation of the heat pipe 110 is that the first and second stages of the PTR 2 are linked thermally during the cooling of the apparatus. At an ambient temperature, the first stage of the PTR has a cooling power of, say, 300 Watts, whereas that of the second cooling stage is around 100 Watts. As the temperature of the stages drops, the cooling power decreases for each, although that of the second stage decreases more severely than that of the first stage, thereby providing an increasing difference in the ratio of their thermal cooling power as the temperature reduces. It will be appreciated that the target apparatus 103 is connected directly to the second stage 102 of the PTR in FIG. 2 and therefore in the absence of the heat pipe 110 (and more specifically its operation since the respective ends are essentially otherwise isolated from each other thermally), the target apparatus 103 would only be subjected to the cooling power of the second stage 102. The heat pipe 110 allows the cooling power of the first stage to assist in the cooling of the target apparatus 103. Crucially, this occurs only during the cooling of the apparatus, and therefore before the nominal base operational temperatures (steady state) of the stages are reached. Furthermore, the advantageous transfer of the cooling power from the first stage to the second stage by the heat pipe is only provided during the cooling down of the apparatus and it is important that this effect ceases before the apparatus reaches the base temperature for steady state operation. The first stage therefore preferably assists in cooling of the second stage until the latter has reached or approaches the base temperature of the first stage. When the cooling power of the first stage is being provided to the second stage, this is caused by the establishment of a temperature-cycle within the heat pipe 110.

This cycle is the same cycle as is described with respect to FIG. 11, namely the condensation from the gaseous phase of Krypton at the upper end 111 of the heat pipe, the dripping of the liquid to the lower end 112 and the heating of this liquid to cause evaporation at the lower end 112. The Krypton gas which has evaporated then travels up the heat pipe 110 to again condense on the surface of the upper end 111.

By virtue of the design, the condensation inside the heat pipe will cease at a predetermined temperature in order to isolate the second stage 102 from the first stage 101. The thermal isolation then allows the second stage 102 to cool further until it reaches its nominal base temperature for steady state operation.

As has been discussed in association with FIG. 1 in particular, the frequency of operation of the mechanical refrigerator (PTR in this case) can be modulated in accordance with the operational state of the mechanical refrigerator, which in particular relate to the temperatures attained by each of the first and second PTR stages together with whether or not the thermal link in the form of the heat pipe is effectively providing a thermal "short circuit" between the two PTR stages. By carefully controlling the operational frequency of the mechanical refrigerator the cooling power may be optimised and directed at the appropriate stage at the appropriate time and therefore the overall cool-down time of the system may be improved significantly.

Figure 3:
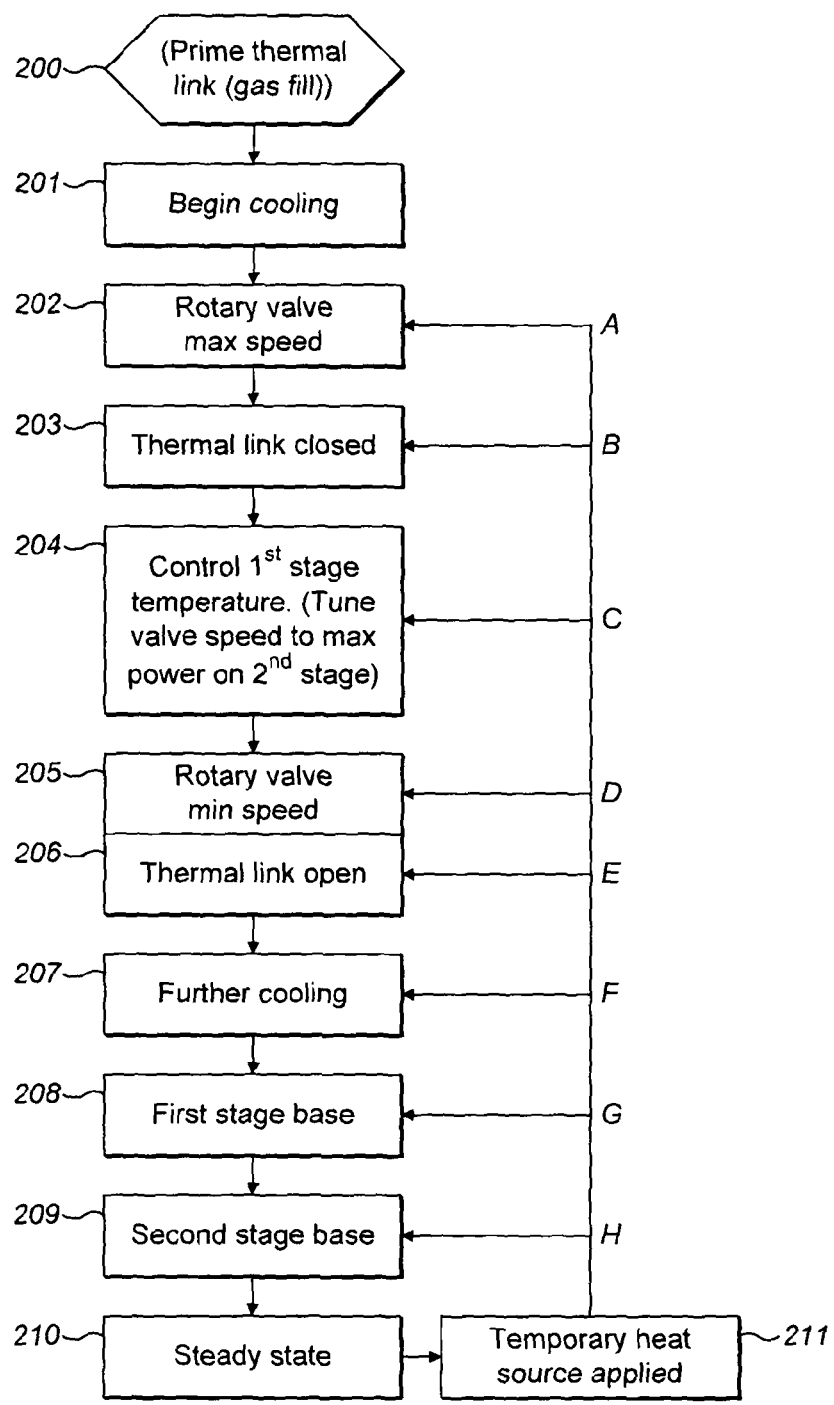
FIG. 3 shows a general flow diagram illustrating the method of use of the examples.

We refer now to FIG. 3 which is a flow diagram of a method of operating the apparatus shown in FIGS. 1 and 2. In addition, reference is made to FIG. 4 in which the temperatures of the first stage 101 (shown as "PT1") and the second stage 102 (shown as "PT2") are plotted schematically on a temperature-time graph. As noted above, the cryogen in the present example is Krypton gas although other gases or mixtures of gases are possible and should be considered by those wishing to practically implement the invention. The method described in FIG. 3 relates to the cooling down of the apparatus from ambient temperature to the operational nominal base temperature by which the steady state operation is effected.

With reference to FIG. 3, initially, the thermal link (which in the present case is the heat pipe 110) is primed by filling with Krypton gas at step 200. In the present case a pressure of approximately three atmospheres is used. It should be noted that Krypton gas has an atmospheric (one atmosphere pressure) boiling point of 120 Kelvin and a melting point of 116 Kelvin.

Figure 4:
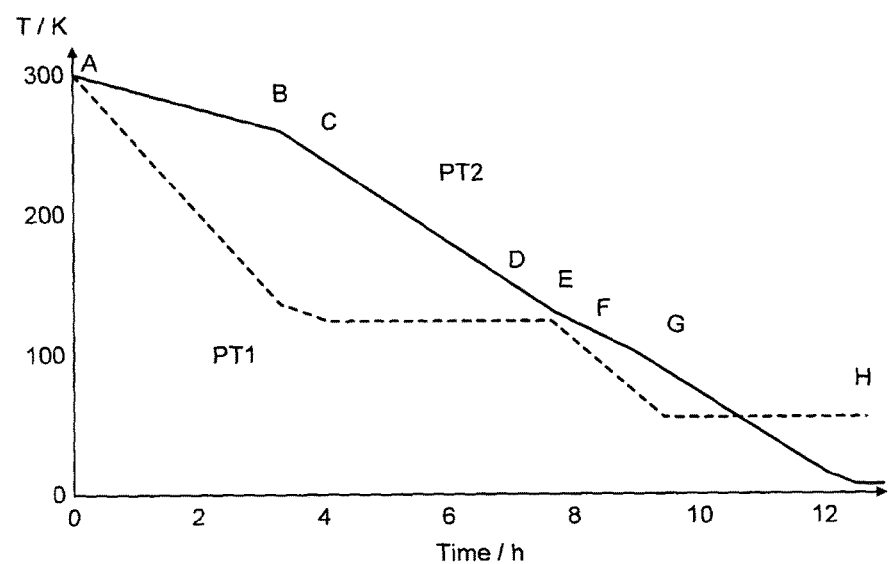
FIG. 4 is a schematic temperature-time curve showing the cooling of the first and second cooled stages of a mechanical refrigerator according to the examples.

The cooling of the PTR begins at step 201. At this stage, the PTR stages are at ambient temperature and the gas pressure within the PTR system is at its highest. For this reason the system controller 5 begins operating the rotary valve 4 at maximum speed (step 202). With reference to FIG. 4, step 202 is represented on the temperature-time graph at point A. As will be appreciated by those of ordinary skill in the art, when operating a PTR such as PTR 2 positioned within a cryostat, the first stage 101 cools significantly more quickly than the second stage 102, particularly if there is a significant thermal mass attached only to the second stage. This is illustrated in FIG. 4 by the relative negative gradients of the curves illustrating the temperature of the first and second stages. For example after a period of around 3.5 hours, the second stage ("PT2") has only cooled by 10 to 20 degrees Kelvin with respect to ambient temperature. In comparison, the first stage ("PT1") has cooled to a temperature of 120 Kelvin which it will be recalled is the boiling point of the Krypton gas. It will also be recalled that the first stage 101 of the PTR 100 is in strong thermal communication with the upper end 111 of the heat pipe 110. Essentially therefore, the upper end is at the same temperature as the first stage. Hence, prior to achieving the temperature of 120 Kelvin for the first stage, the heat pipe is effectively disengaged and is not operating as a thermal link although there may be some relatively minor cooling effect of the second stage caused by convection.

Whilst the system controller 5 does cause the rotary valve 4 to decelerate during this period as the helium gas within the PTR cools, the majority of the cooling power of the system is used to cool the first stage of the PTR during this period and little is used to cool the second stage, despite the appreciably larger thermal mass which may be in thermal communication with the second stage. We note here that, in general, the pressure monitored within the high pressure line is desired to be as close to its operational maximum as possible throughout the cooling process so as to maximise the efficiency of the PTR cooling effect. The system controller 5 effects this in response to pressure readings taken from the pressure sensor 6.

At point B in FIG. 4, the 120 Kelvin temperature is attained by the first stage 101. The heat pipe begins to operate at this temperature and effectively causes a closed thermal link to be in place between the first and second stages (see step 203 in FIG. 3). At this temperature the Krypton gas within the heat pipe 110 begins to condense upon the surface 114. Thus the condensation process starts and this provides a significantly increased cooling power to the second stage by virtue of the cold liquid dripping from the upper end 111 to the lower end 112 of the heat pipe 110. The transfer of the cooling power from the first to the second stage causes an enhanced negative gradient in the second stage cooling curve in FIG. 4 and also a consequential increase (less negative) in the gradient of the first stage.

As will be explained further with reference to FIG. 5, the system controller 5 uses temperature measurements from one or more thermocouples in the region of the heat pipe to monitor when the heat pipe is at its operational temperature. Such temperature measurements could be made indirectly using pressure measurements which may need to be calibrated for different application systems where the PTR is used. Assuming they always follow the same cool-down curve, then pressure is a valid measurement of when the heat pipe is active. The objective during the operation of the heat pipe is to maximise the cooling power delivered to the thermal mass coupled with the second stage of the PTR. In practice if the same controlled cooling regime is followed during the operation of the heat pipe as is used at higher temperatures (prior to point B) then it is observed that the first stage of the PTR cools below the freezing point of the Krypton gas sooner than desired. This is because, as the second stage cools further, the heat load on the first stage will decrease. This freezing out of the krypton causes the "opening" of the thermal link as the heat pipe operation ceases. It is therefore advantageous to modify the PTR cooling regime adopted during the operation of the heat pipe so as to prolong the operation of the heat pipe and therefore delay the point in time when the freezing of the Krypton occurs.

The modification of the cooling regime is effected at step 204 in FIG. 3. In the present example, subject to the condition that the measured temperature is within a predefined range, the rotary valve speed is modified to a predetermined tuned value which maximises the cooling power at the second stage of the PTR at the expense of that at the first stage. The general concept of tuning of PTRs and other mechanical refrigerators is generally understood by those of ordinary skill in the art. For example tuning is typically used when initially setting up a PTR for the first time. In a PTR there is a complex relationship between the magnitude, frequency and phase of the high and low gas pressures applied to the PTR and the resultant effect upon the cooling power achievable at the first and second stages. Whilst tuning upon initial PTR setup may involve the setting of gas impedances in certain gas lines, in the present example the "tuning" used at step 203 is only concerned with the PTR operational frequency. The frequency (rotary valve speed) is held at a predetermined constant value (this being the result of tuning experiments) during the operation of the heat pipe, at a frequency which promotes the cooling effect at the second stage and also weakens the cooling power at the first stage so as to prolong the operation of the heat pipe. This is illustrated at C in FIG. 4 where the temperature of the first stage stops reducing and remains approximately constant due to the heat being transferred by the heat pipe from the first to the second stage.

As can be seen from FIG. 4, during the operation of the heat pipe, the temperature of the second stage is in excess of 120 Kelvin and therefore the liquid arriving at the lower end of the heat pipe is heated and evaporates, this then travelling back to the upper end for further condensation. As is shown in FIG. 4, the second stage therefore undergoes accelerated cooling (a more negative gradient of the temperature-time curve) whereas the temperature of the first stage remains approximately constant. It should be noted that, as an alternative to the operation of the PTR at a constant frequency at step C a similar effect may be achieved using a heater mounted to the upper end 111 of the heat pipe. This is illustrated schematically at 116 in FIG. 2. However, the use of a heater is less advantageous due to the extra heat load introduced to the system as a whole. It will be understood that the use of a constant operational frequency or a heater are advantageous, although not essential, and therefore may be absent in certain practical applications. In order to exact control over the above process, the system controller 5 is utilised as is shown in FIG. 2, this being connected to the PTR 2 and the heater 116 (if present). The initial control is based on the first stage temperature. There may be an advantage in also measuring the second stage temperature to allow point E (see below) to be detected, in which case a thermocouple is provided for measuring the temperature of the Krypton in the lower part of the chamber of the heat pipe adjacent the lower end 112 (not shown in FIG. 2). This also feeds a signal to the system controller 5.

Returning now to FIGS. 3 and 4 and the description of the method, the operation of the PTR at a constant frequency persists during step 204 whilst the measured temperature at the heat pipe is within the predetermined range. During this process the temperature of the second stage reduces which in turn causes a reduced heat load on the first stage. The cooling then reverts to the previous frequency dependent control once the temperature of the lower part of the heat pipe falls outside of the range and the system controller 5 gradually slows the rotary valve 4. In the example shown in FIG. 3, the rotary valve speed then reaches a predetermined minimum at step 205, this being the optimum speed for cooling the second stage to its lowest temperature. This is shown at point D in FIG. 4. In this case the rotary valve speed reaches its minimum before the heat pipe falls below its minimum operational temperature at step 206 (at which point it becomes an open thermal link). Once the first stage reaches 116 Kelvin at point E, the liquid Krypton will solidify at the upper end of the heat pipe and the thermal link becomes open. It will be appreciated that point D may occur after point E in FIG. 4 depending upon the system design.

Thereafter, each of the first and second stages cool further at step 207 (shown at F in FIG. 4). The first stage reaches its operational nominal base temperature at step 208 (G in FIG. 4) after just over 9 hours, notably earlier than the attainment of the base temperature by the second stage. An example nominal base temperature is 50 Kelvin for the first stage. As is shown in FIG. 4, the second stage eventually reaches its nominal base temperature after around 12 hours at point H, such as 4.2 Kelvin or lower (step 209). Finally, the target apparatus reaches its operational temperature once the second stage is cooled to its base temperature and then the apparatus is ready for steady state operation which is illustrated at step 210.

As will be appreciated, the heat pipe will only accelerate the cooling between points B and E of the graph shown in FIG. 4. In particular it will not provide this function at temperatures either above or below these points (save for the natural convection of gas in the pipe at elevated temperatures). For this reason it may be advantageous to use a mixture of gases with different melting and boiling points inside the heat pipe 200 (or equivalent multiple heat pipes, each with its own coolant) which would aid the cooling at higher and/or lower temperatures and therefore provide a greater operational temperature range.

In the ideal case, all the cooling power of the first stage at point B will be added to the cooling power of the second stage. In the case of the use of a coolant such as Krypton in a heat pipe integrated into a pulse tube refrigerator, this would equate to an additional 150 Watts of cooling power. In comparison, the average cooling power between points B and E without a heat pipe and without frequency control on the PTR rotary valve would be less than 75 Watts. Thus, the invention provides the ability to more than double the cooling power within the operational range of the heat pipe in practical applications. It will be appreciated that in the event of the heat pipe containing multiple gases, each operating over a different temperature range or in the event of multiple heat pipes in parallel each operating over different temperature ranges, that in FIGS. 3 and 4, points B to E may optionally be repeated at the optimum cooling temperature for each of the heat pipe gases.

Figure 5:
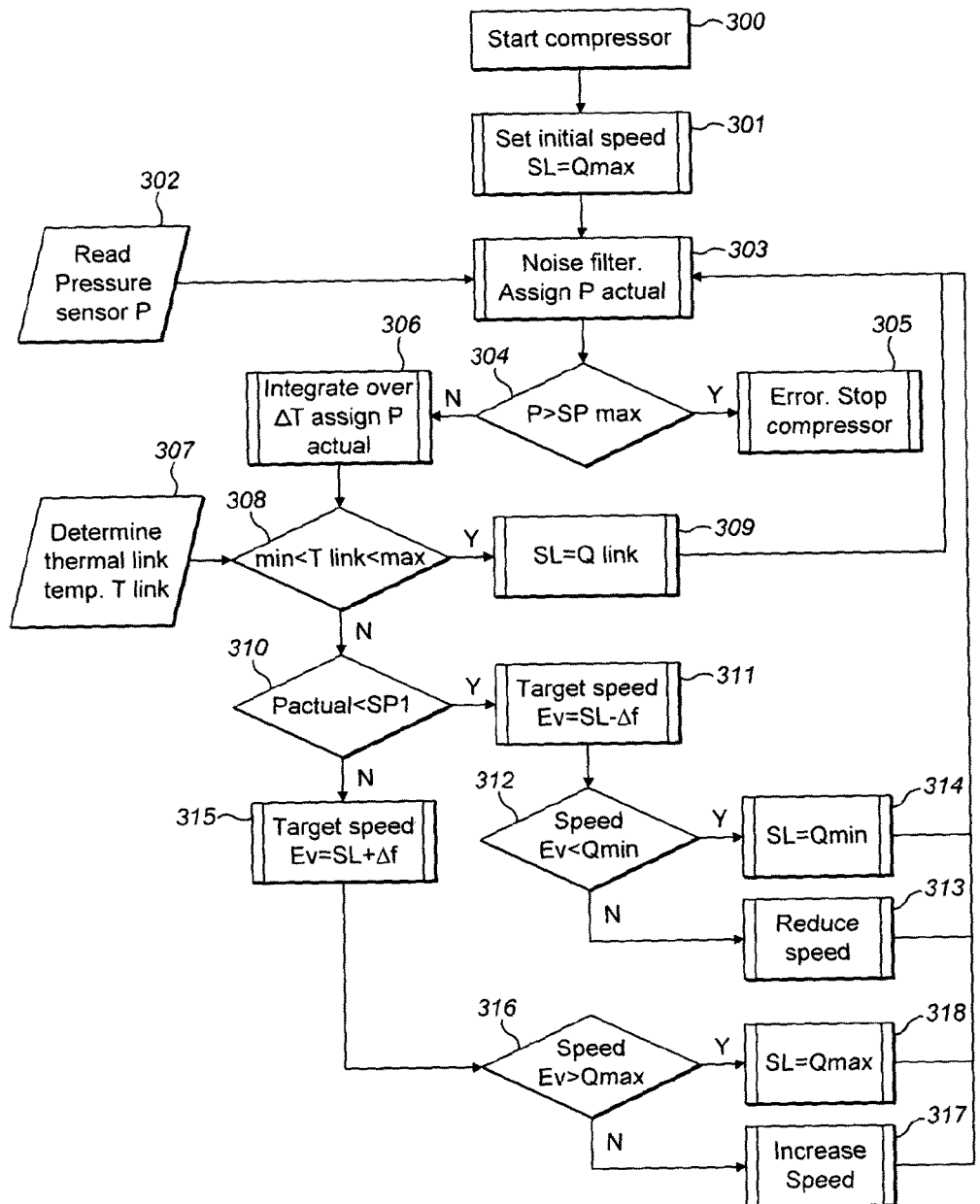
FIG. 5 shows a flow diagram illustrating the operation of the apparatus.

Referring now to FIG. 5, the operation of the system as shown in FIG. 2 is described in more detail with reference to the control of the operational pressure and rotary valve speed.

At step 300 the compressor 1 is started and the compressor motor 8 is initiated. At step 301 the system controller 5 rotates the rotary valve 4 at a speed ("SL") which is a maximum for the PTR 2 in question. This value is denoted "Qmax" in FIG. 5. At step 302 the signal from the pressure transducer 6 is sampled and noise filtered and/or averaged by an algorithm, the sampling being at a rate of a few milliseconds. At step 303 a first pressure reading is evaluated by converting the averaged/noise filtered pressure signal over a number of counts into a pressure reading, denoted "Pactual". At step 304 Pactual is compared with a predetermined set point value (denoted "SPMax"). If the pressure Pactual is greater than SPmax (which might be typically 410 psi or 2.83 MPa) then the compressor is automatically stopped at step 305 and a fault code is displayed. Such failure typically occurs when the high pressure line is not connected to the rotary valve 4 or is blocked, or if the rotary valve is not rotating.

If however the pressure is lower than the set point pressure of 410 psi (2.83 MPa) then at step 306 a second algorithm is used in which the system controller 5 begins taking monitored pressure readings at a predetermined sampling rate. The pressure measurement is averaged over at least one full cycle of the rotary valve in order to create a mean pressure measurement. This is because the pressure cycles up and down each time the valve opens and closes. The algorithm converts a rolling average of pressure values from the pressure transducer 6 and assigns the evaluated value to Pactual.

At step 307 a temperature measurement ("T link") is taken from the heat pipe thermocouple (the heat pipe acting as a thermal link). At step 308 it is evaluated whether the temperature measurement falls within a predetermined temperature range between a minimum temperature ("min") and a maximum temperature ("max"). If the outcome of the evaluation at step 308 is that the measured temperature does fall within this range then the speed is set to a predetermined constant ("Q link"). This effects step 204 in FIG. 3. If the outcome of the evaluation is that the temperature does not fall within the range then the method proceeds to step 310.

At step 310 Pactual is compared with a set point pressure SP1. SP1 may optionally change during the cool-down either based on recent pressure history or based on another measurement such as a direct temperature. An algorithm may determine SP1. In this case however, SP1 is a single pressure value slightly less than the maximum pressure (SPmax) allowed by the compressor design (SP1 is for example 400 psi, 2.76 MPa). It is desirable to operate the PTR, when possible, at the highest safe pressure which can be thought of as SP1, this allowing the maximum cooling power of the PTR 2. As the PTR 2 cools the speed of the rotary valve 4 required to maintain the high pressure close to SP1 gradually decreases. For this reason a gradual slowing of the rotary valve 4 is desired. This is achieved by monitoring the pressure Pactual.

At step 311, which occurs if the average pressure Pactual is less than the set point pressure (SP1), then a reduction in speed of the rotary valve 4 is desirable. At step 308 an evaluated speed Ev is calculated. This is calculated as the current speed (SL) reduced by an amount "Δf" representing a decremental change in the speed. This evaluated speed is compared with a speed Qmin at step 312. Qmin is the optimal speed in the "cold condition" for the PTR 2 (that is the speed used at the base temperature). If the evaluated speed Ev is not less than Qmin then the reduction in speed is assigned as the new speed SL at step 313. Having reduced the speed the algorithm returns to step 303 and repeats.

If the evaluated speed Ev at step 308 is less than Qmin, then at step 314, the speed SL is set to Qmin and the algorithm loops back to step 303.

The other alternative at step 310 is that the pressure Pactual is not less than SP1. In this case it is desirable to increase the speed of the rotary valve 4. A similar calculation is then performed at step 315 to that performed at step 308, namely, calculating the evaluated speed, Ev. Here the evaluated speed is then compared with a speed Qmax at step 316. Qmax is the maximum speed of operation of the rotary valve 4 which in turn is set by the maximum operational speed of the PTR 2.

At step 317, if the evaluated speed Ev is not greater than Qmax then an incremental increase of the speed (SL) to Ev is effected. The algorithm then loops back to step 303.

If the evaluated speed Ev is greater than Qmax, than a step 318, the speed SL is set at Qmax and the algorithm again loops back to step 303.

Whilst the focus of the present example is in the cooling cycle of a closed cycle refrigerator such as the PTR 2, it is also notable that such a process as described above also works during a warming procedure from the base temperature. This is illustrated in FIG. 3 where step 211 illustrates how the application of a heat source for a temporary period can cause heating of the system and return the system to one of the states A to H in FIG. 4. Furthermore, whilst FIG. 5 was discussed with the use of a thermocouple providing temperature information from the thermal link, in practice the value of "T link" may alternatively be replaced by indirect calibrated pressure measurements.

There are a number of different practical means by which the algorithm which governs the process of FIG. 5 may be implemented. In FIG. 5, values for "f" may be calculated by the equation: f=c (Pactual−SP1) where c is a constant. This ensures that the magnitude of change in the speed which may be effected during each process loop is proportional to the difference between the actual pressure (Pactual) and the desired pressure (SP1).

It will be appreciated that the illustrative example of FIG. 5 can be easily effected via look-up tables. A more advanced system having effectively a continuum of temperature-pressure regimes can of course be contemplated and effected either via a corresponding number of table entries in a look-up table or via a calculation according to a linear or polynomial approximation for example. This may include the use of additional considerations for optimising the performance of the system, such as in reducing vibrations.

Figure 6:
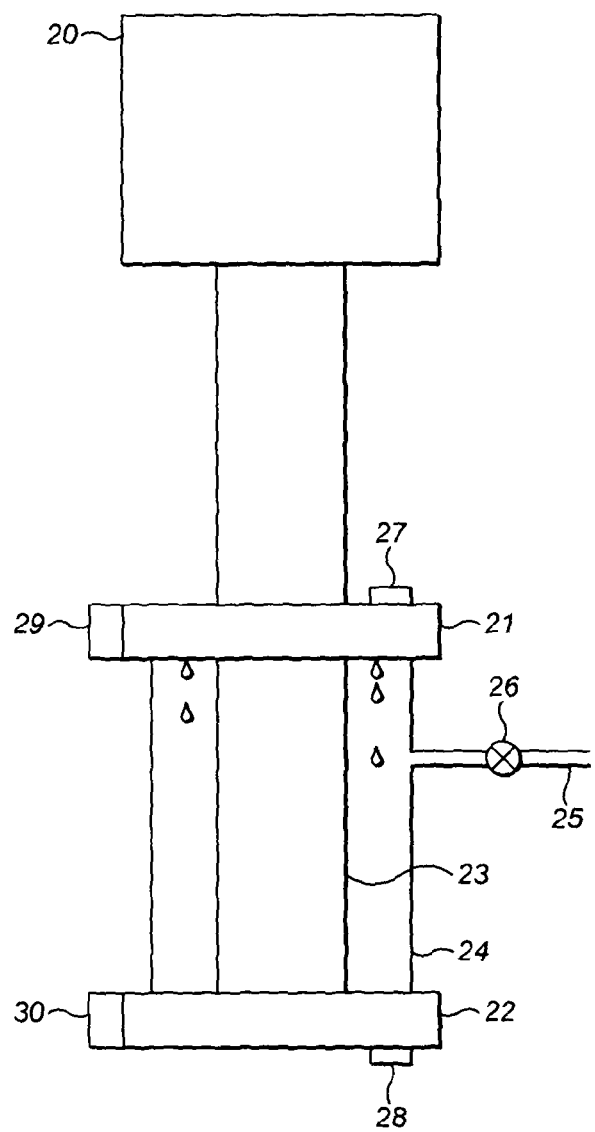
FIG. 6 shows a second example apparatus incorporating a heat pipe.

A second example apparatus is illustrated in association with FIG. 6. In this example a two stage Gifford-McMahon cryocooler 20 performs the function of the mechanical refrigerator. Here, as for the PTR discussed in association with the first example, first 21 and second 22 cooled stages are provided, each having a thick high conductivity copper plate for thermal coupling with other components. As for the PTR 2 of the first example, ultimately when in steady state operation the first stage 21 is cooled to a temperature which is higher than the second stage 22. As is illustrated in FIG. 6 the second stage of the cooler, including its associated tube 23, is surrounded concentrically by a thin stainless steel tube 24. In use this concentric tube acts as a heat pipe and is filled through a filling line 25 via a valve 26 with neon gas (or any other appropriate gas). The concentric tube is sealed at each end, with a gas-tight seal, to the respective copper plates of the first and second cooled stages. Thus, the concentric tube, in cooperation with the second stage tube which it surrounds, forms a vessel which surrounds and is in good thermal contact with the second stage tube.

As will be appreciated, in much the same way as a PTR, GM cryocoolers are operated by the application of cyclical gas pressure in order to force a piston (sometimes referred to as a displacer) along the cooler in a reciprocating manner. In an analogous manner to the use of the coupling element to control the operational frequency of a PTR, the piston may also be driven in a similar manner at a controllable frequency. FIG. 6 illustrates schematically how each stage of the GM cryocooler is equipped with a thermocouple (27, 28). Signals from these thermocouples are monitored by the control system (not shown in this figure) in order to control the frequency of operation of the GM cryocooler.

The heat pipe is used to thermally link the first 21 and second 22 cooled stages. In particular, because the cooling power deliverable to the first stage is higher than that deliverable to the second stage, it is desirable to thermally link or "short" the first and second stages such that any thermal mass in thermal communication with the second stage may be cooled by the higher cooling power of the first stage.

The heat pipe is therefore operable during an initial cooling stage in which the first and second stages are cooled down from room temperature towards the steady state temperature of the first stage. We note here that the steady state temperature of the first stage 21 may be lower than the freezing point of the gas within the heat pipe depending upon the type of gas used, it's operational pressure and the steady state temperature desired. A supplementary heat source may be provided to each stage (using heaters schematically indicated at 29,30) in order to prevent any freezing of the gas within the heat pipe, in which case step 307 to 309 in FIG. 5 are modified accordingly. Again, as an alternative, a modification of the operational frequency of the cryocooler may be utilised to prolong the effect of the heat pipe. During this stage the GM cryocooler frequency is driven to maximise the cooling of the first and second stages together. In this regime the GM cryocooler is therefore operated at a frequency which favours maximising the cooling power of the first stage. This cooling regime persists during the operation of the heat pipe, even though more of the cooling power is transferred to the second stage 22 due to the thermal link provided by the heat pipe.

As each stage cools, with the second stage temperature being initially higher than that of the first stage, typically some time after the operation of the heat pipe has finished (caused by the coolant becoming solidified), the second stage 22 eventually attains a similar temperature to that of the first stage 21 as the first stage approaches its base temperature. At this point a different cooling regime is adopted whereby the operational frequency of the GM cryocooler is reduced in order to optimise the final temperature of the second stage. In regions B to E of FIG. 4 where the heat pipe is operating, cooling power is optimised on the second stage so as to reduce cooling power on the first stage and minimise the amount of heating required to keep the heat pipe operating. After point E, the frequency is adjusted to that which gives the lowest base temperature, which may be different to that which gives the max second stage cooling at 100 degrees K. This may be readily achieved using a computer controller acting upon temperature feedback from the cooled stages or from the pressure within part of the GM cryocooler, or each of these.

Figure 7A:
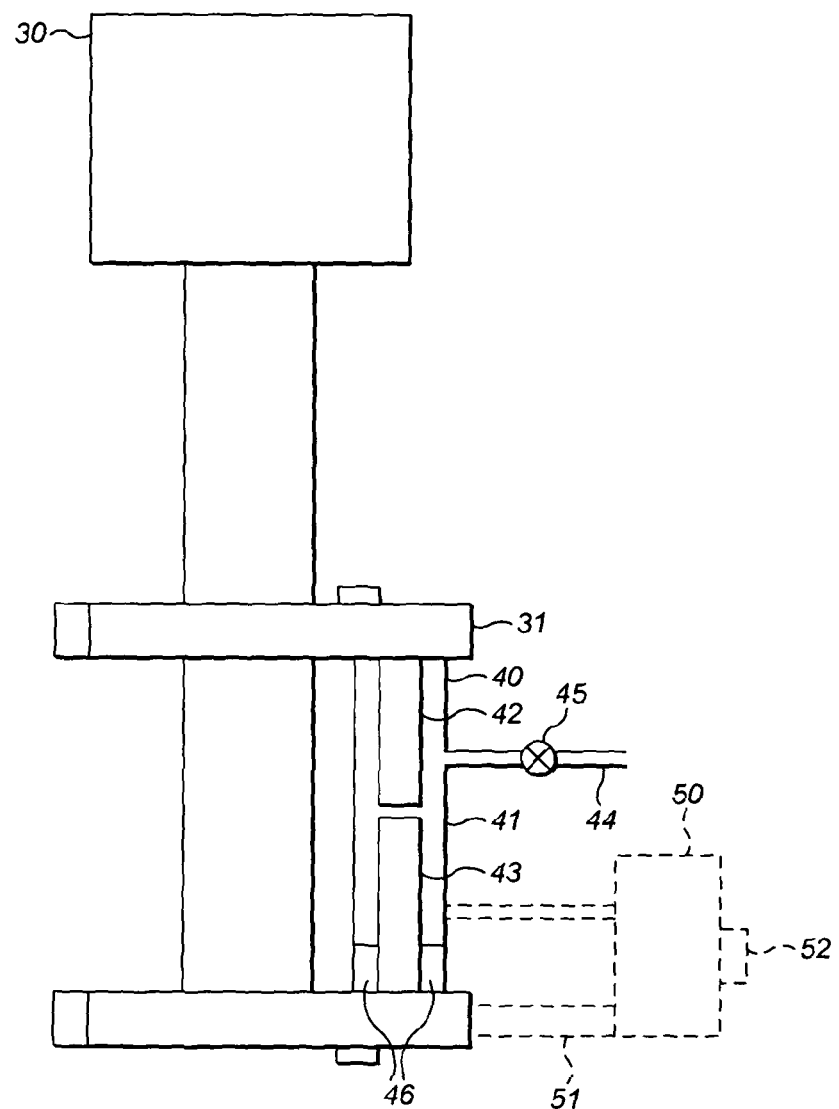
FIG. 7A shows a third example apparatus incorporating a heat switch.

A third example is illustrated in FIG. 7A. Unlike in the previous examples which have utilised heat pipes, in the present example the thermal link is provided by the use of a "gas gap heat switch". A gas gap heat switch utilises the heat transfer properties of certain gases, particularly over very short distances, to effect an engageable thermal link. In its simplest form a gas gap heat switch comprises two, high thermal conductivity surfaces which are brought into close approach but do not make physical contact under operational conditions. Aside from relatively minor thermal radiation transferring across the gap between the surfaces, if the environment between the surfaces is evacuated then little heat transfers across the gap between the two surfaces. In this condition the gas gap heat switch can be thought of as "OFF" or "disengaged" and this occurs if the gas between the surfaces is at a sufficiently low pressure that it is in the so called "molecular" regime. If a gas is then introduced between the surfaces then a relatively high heat transfer can be achieved across the gap provided an appropriate pressure regime is used which causes to the gas to adopt the "viscous" regime. Different gases may be used to achieve this effect including neon, xenon and helium (including He-3 and He-4) for cryogenic applications. The gas may be introduced or evacuated from the gap between the surfaces by a suitable pumping system. However, in the case of cryogenic applications it is advantageous to use adsorbent material in combination with a suitable heating and cooling system to modulate the gas pressure. This is advantageous since it allows the gas gap heat switch to be operated without any mechanical moving parts.

FIG. 7A illustrates how a gas gap heat switch may be utilised to effect the thermal link within the present example. In this case a PTR 30 is provided with a gas gap heat switch 40 located between the first 31 and second 32 cooled stages. In a somewhat analogous manner to the previous example the gas gap heat switch is embodied by a stainless steel tube 41 located between the first and second stages of the PTR 30 and sealed with gas-tight seals to each of the high conductivity copper plates of the respective stages. A first rod 42 formed from high thermal conductivity copper is positioned within the stainless steel tube and projects from the first cooled stage towards the second cooled stage. Similarly a second high thermal conductivity copper rod 43 projects from the second stage towards the first stage. The respective ends of the rods are formed into faces which are aligned in an opposing manner and which are separated by a small gap. Preferably the opposing ends are formed as high surface area components such as being provided with castellations which conform with each other so as to increase the area of opposing surfaces between the rods. In practice the respective surfaces may come into contact when at ambient temperature, with the gap between them only forming at lower temperatures. This may be advantageous in that it may maximise the cooling effect at high temperatures by providing a physical conductive contact between the rods. A filling line 44 is provided to allow the initial charging, through a valve 45, of the gas gap heat switch 40 with a predetermined amount of gas at a pressure which is typically in excess of 1 atmosphere. In the present case neon is chosen as a suitable gas. A mixture of neon and xenon may also be used to beneficial effect.

At the end of the stainless steel tube within the gas gap heat switch, next to the second stage copper plate and surrounding the rod which projects towards the first stage, an amount of activated charcoal 46 is provided to act as an adsorption material. The charcoal has the property of adsorbing the neon as a function of temperature. At a relatively high temperature such as 150K very little adsorption occurs and the pressure is such that the "viscous" regime of high thermal transfer is possible between the rod surfaces. At low temperatures such as below 40K the adsorption capacity of the charcoal increases dramatically and causes the pressure of neon or neon/xenon mixture to decrease into the "molecular" regime.

Thus by modulating the temperature of the charcoal the gas gap heat switch 40 can be caused to adopt an "ON" or "OFF" state selectively. In the present case the cooling "mode" adopted by the system controller is selected based upon the pressure monitored within the high pressure side of the gas circuit and which is indicative of the average temperature in the PTR circuit. As in the previous example, when the adsorbent charcoal is relatively warm and the neon pressure is high causing the gas gap heat switch to be "ON", the first and second stages are thermally shorted and the controller operates the PTR at a relatively high frequency in order to provide rapid cooling to the first and second thermally coupled stages. The neon exchange gas remains in the gaseous state within the gas gap heat switch 40 until the second stage cools to a temperature low enough to strongly adsorb the gas within the charcoal adsorber 46 and reduce the pressure of the gas within the switch and therefore remove the heat flow path between the rods. Later, at a stage following the decoupling of the thermal link between the two stages as provided by the gas gap heat switch, the controller reduces the operational frequency of the PTR so as to adopt a cooling regime in which cooling of the second stage is optimised and the second stage cools to its base temperature, substantially colder than that of the first stage.

The presence of the adsorption material 46 within the gas gap heat switch provides a self-contained automatic system which operates in a predictable manner as a function of temperature. In order to provide for increased operational flexibility, the adsorbent material may be provided within a separate chamber 50, rather than in the confines of the stainless steel tube. In this alternative, as indicated by dashed lines in FIG. 7A, the separate chamber may be provided in weak thermal communication with the second cooled stage (so as to provide the cooling effect necessary for causing adsorption) through a weak thermal link 51. Advantageously, the chamber 50 may be provided with a small heater 52 (under the control of the controller) which may be used to maintain the gas gap heat switch in the "ON" state when the temperature of the second stage drops below the efficient adsorption temperature of the exchange gas. Hence the heater 52 is used to keep the heat switch operational despite the drop in temperature of the second stage below the temperature at which the gas gap heat switch would otherwise remain "ON". A practical limit to this would be when the gas condenses upon the gas gap heat switch surfaces. We note here also that the heater 52 itself could be controlled in response to a reference temperature of either the first or second stages (or each of these), or with reference to a monitored pressure within the PTR (as is used to control the frequency of the PTR).

Figure 7B:
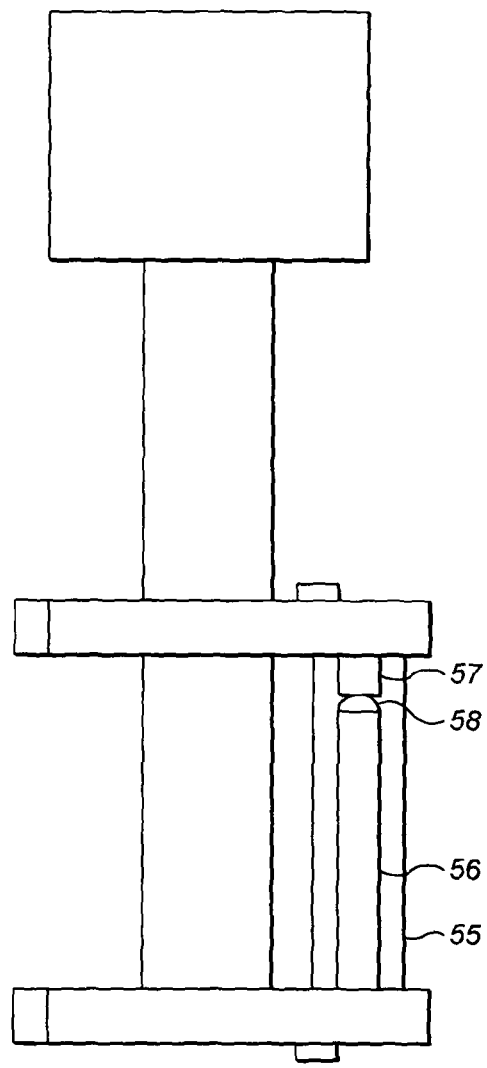
FIG. 7B shows a fourth example apparatus incorporating a mechanical thermal link.

FIG. 7B shows a further example somewhat analogous to FIG. 7A, where the gas gap heat switch is replaced by a thermally expandable link. Here a stainless steel tube 55 located between the first and second cooled stages encloses a high thermal conductivity rod 56 projecting from the second cooled stage towards the first cooled stage. A short rod 57, again of high thermal conductivity material such as copper, projects from the first stage towards the end of the rod 56. A pre-loaded high thermal conductivity spring 58 attached to the end of the rod 56 bridges the gap between the opposing ends of the rods and makes a good thermal contact between them. The spring is preloaded such that when the stages cool and the rods contract axially, the spring 58 expands so as to maintain the thermal connection for a range of temperatures. Thus at room temperature the rods are thermally in contact via the preloaded spring. As the temperatures of the stages drop and the rods contract the end of the rod 56 moves away from the opposing end of the rod 57, the unloading of the spring 58 causes it to extend, thereby maintaining the thermal contact. However, upon further cooling the spring becomes fully unloaded and at lower temperatures the thermal link is broken as the spring separates from being in contact with the rod 57. By a careful selection of the spring and preloading force the thermal link may be effected from room temperature down to a desired predetermined temperature. As for other examples, the temperature of parts of the system, or the pressure response, may be monitored to evaluate when such a link has been opened and the cooling modes of the cooler may be modified accordingly. It will be appreciated that, as for the other examples of thermal links, this mechanical link is equally applicable to PTR, GM and other cryocoolers.

Figure 8:
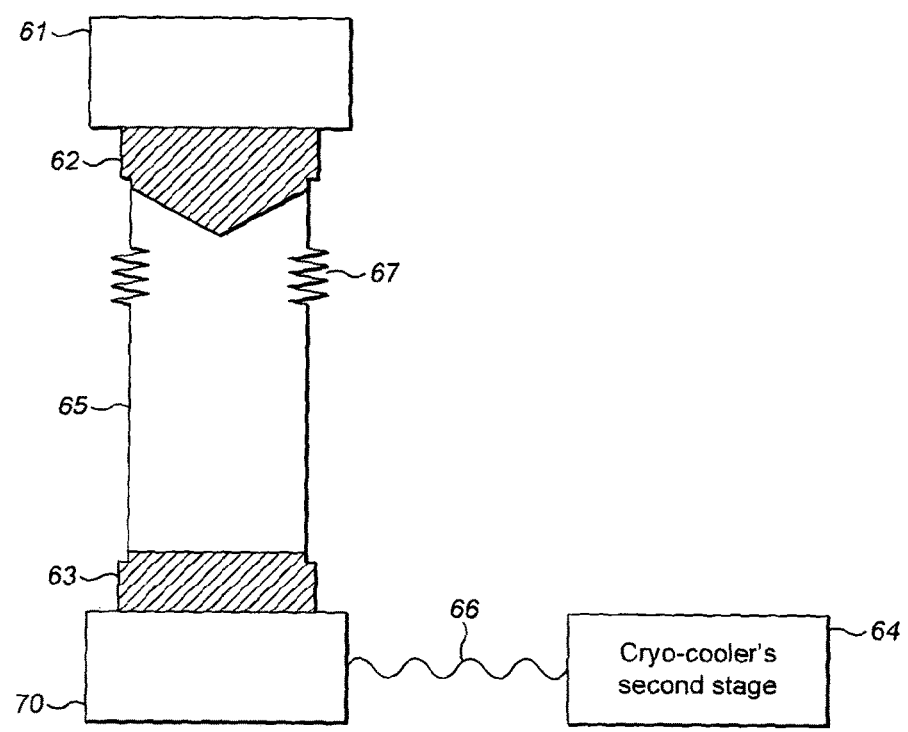
FIG. 8 shows an example heat pipe with anti-vibration features.

FIG. 8 illustrates a further example arrangement which may be used with a PTR, GM or other cryocooler. In this example, a first stage 61 of a PTR has a lower surface to which the upper end 62 of a heat pipe 65 is connected directly. Furthermore, target apparatus 70 is connected directly by a suitable mounting to the lower end 63 of the heat pipe 65. This example includes anti-vibration features. The first of these is shown at 66 where an anti-vibration coupling separates the target apparatus 70 (in this case an experimental payload) from the second stage 64. This coupling 66 may take the form of copper braid. Such a mechanism is useful when the experimental payload of the target apparatus 70 is sensitive apparatus such as a superconducting magnet. This is especially important where the payload is a superconducting magnet for an MRI imaging system, where, in addition to improving image resolution, there is a desire to reduce vibrations and audible noise since it is well established that many MRI procedures are aborted by patients when they become distressed during such procedures.

The high conductivity braid, which is typically formed of copper, prevents the transmission of vibrations to the experimental payload. A further aspect of this anti-vibration example is the presence of edge-welded bellows 67 within the wall of the heat pipe 65. This allows the heat pipe to connect directly to the PTR's first stage without the target apparatus 70 being subject to unacceptable vibrations. As will be appreciated, without the presence of the edge-welded bellows 67, vibrations would be able to propagate relatively easily along the heat pipe thus bypassing the anti-vibration coupling 66 between the second stage in the experimental payload of the target apparatus 70. The thermal benefit of the use of the heat pipe during cooling is even greater in this example since the anti-vibration couplings generally reduce the available cooling power of the second stage by as much of a factor as two due to a temperature gradient forming across the coupling when in use. Therefore the provision of at least an additional 150 Watts (in the case of a PTR) from the first stage will be even more noticeable.

Figure 9:
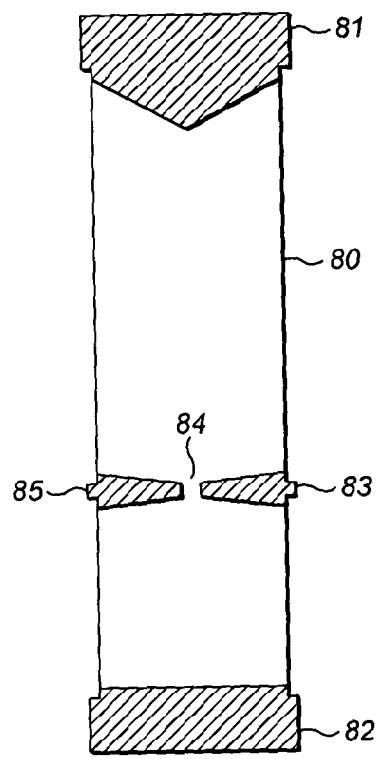
FIG. 9 illustrates the provision of an anti-radiation member within the heat pipe as a further example.

FIG. 9 shows yet a further example heat pipe apparatus. The heat pipe 80 has an upper end 81 and a lower end 82. In addition however an anti-radiation member 83 is positioned intermediately between the upper and lower ends. The anti-radiation member 83 takes the general form of a disc which, in the case of a right circular cylindrical heat pipe 80, is circular in form and of approximately of similar radius. The disc is provided with a small central orifice and the thickness of the disc reduces generally linearly towards its central orifice position. The anti-radiation member 83 is arranged within the heat pipe 80 such that the axis of the heat pipe passes through the orifice and is approximately parallel to the plane defining the disc. The tapering of the thickness ensures that an upper surface of the anti-radiation member 80 which receives liquid condensate from the upper end 81 above, causes the liquid to flow towards and pass through the orifice. The orifice is illustrated at 84 in FIG. 9.

At least part (a peripheral portion) of the anti-radiation member 83 is arranged to pass through the walls of the heat pipe 80 so as to allow thermal connection to the second stage of the PTR at a point illustrated at 85. The purpose of the anti-radiation member with associated small orifice is to reduce the thermal radiation from the upper end of the heat pipe. This is particularly useful in applications where the experimental payload of the target apparatus consists of a secondary refrigerator system such as a dilution refrigerator or a helium-3 refrigerator which is very sensitive to thermal radiation. The orifice typically is a few millimeters in diameter which is small enough to prevent most of the radiation from passing between the ends, but not so small as to restrict the flow of liquid or gas. The thermal linking of the second stage to the anti-radiation member allows for the target apparatus to be at a lower temperature than that of the second stage. This will cause the cooling of the second stage and also of the target apparatus during the cooling cycle.

Application to Magnetic Resonance Imaging Systems

Figure 12:
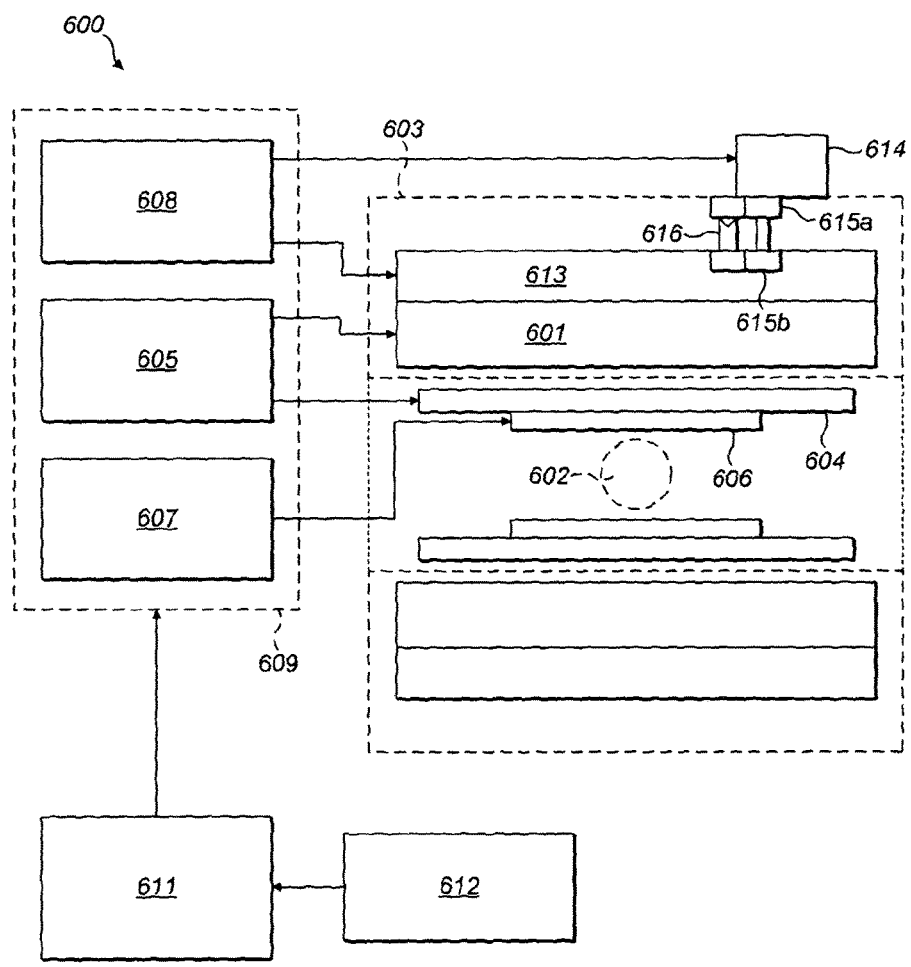
FIG. 12 is a schematic diagram of a magnetic resonance system incorporating a cryogenic cooling apparatus according to the examples.

FIG. 12 illustrates an example arrangement where a PTR of the form discussed earlier is used to provide cooling power to a magnetic resonance imaging system. However, the skilled person will appreciate that a GM or other cryocooler as discussed above may be used to provide such cooling power. The magnetic resonance imaging system 600 includes a primary magnet system 601. The primary magnet system 601 includes a main field magnet arranged in the form of superconducting coils wound on a former in a solenoid arrangement. It will be understood that other magnets are present within the system for ensuring magnetic field correction, including shimming magnets, to ensure that the magnetic field generated within a target region of interest 602 within the centre of the solenoid arrangement is sufficiently highly homogeneous in order to produce highly spatially resolved signals. In a medical environment, part of the body of a patient to be investigated is positioned within this target region 602. When in use, the superconducting coils are maintained below their superconducting transition temperature by placing them in thermal contact with a heat sink of some kind, and ensuring they are held in a cryostat 603 which provides a highly thermally insulated environment.

According to the principles of MRI, the spatial information from within the target region is obtained by analysing radio-frequency (RF) signals received from material within the target region when such a region is subjected to magnetic field gradients. The magnetic field gradients are generated by gradient field coils 604 under the control of a magnet controller 605 which controls the gradient field coils 604 and the primary magnetic field system 601. The gradient coils produce magnetic field gradients in three orthogonal directions using resistive magnets since the field strength required is much lower. It is advantageous to place the gradient field coils 604 close to the target region and therefore within the solenoid bore. Similarly, an RF transmitter/receiver 606, which transmits and receives radio frequency signals from the target region is advantageously placed close to the target region 602, again, as shown in FIG. 12, within the solenoid bore. The transmitter/receiver 606 is controlled using an RF controller 607. A cooling system controller 608 controls the cooling of each cooled component of the MRI system 600, such as the primary magnetic field system. The magnet controller 605, RF controller 607 and cooling system controller 608 are in turn each operated as part of a system controller 609.

As will be understood by those of ordinary skill in the art, the formation of meaningful imaging data from the RF signals received from the target region under the respective gradient conditions requires advanced and substantial computational resources. These are provided within the present example system by the image acquisition and processing system 611. The example system in practice will include other components and apparatus, for example including patient monitoring, safety monitoring, data storage and more. Each is not shown in FIG. 12 although will be understood to be present. The skilled operator of the MRI system controls the system through the user interface 612. As will be understood, the controllers and other apparatus described above are generally implemented using computer software and electronics.

We turn now to the cooling system itself which is shown at 613 in FIG. 12, this being under the operational control of the cooling system controller 608. As an example of an implementation of the cooling system 613, the magnetic field coils of the superconducting primary magnet system 601 are placed in contact with a heat sink by being surrounded by liquid cryogen such as helium-4. In a practical implementation of a high-temperature superconductor used for the primary magnet windings, then the coolant could be a different liquid such as nitrogen. In the present example the low temperature superconducting coils are immersed within a reservoir forming part of the cooling system 613. The liquid cryogen absorbs heat over time and this causes boil-off into a head space within an upper region of the cooling system 613. The cooling system 613 provides cooling power through the use of a PTR of the form discussed earlier, namely having a control system adapted to modulate the frequency of the cyclical gas pressure, and a heat pipe. However, GM or other cryocoolers may be used, and other thermal links such as a heat switch or mechanical link may be used. The PTR is shown generally at 614. In this case a two stage PTR is used and the first (higher temperature) stage 615a is connected to radiation shield provided within the cryostat. The second stage, shown at 615b, is positioned within the interior of the reservoir within the head space mentioned above. Thus, the gaseous boiled-off helium is recondensed by the second stage of the PTR (since its operational temperature is below the condensation point of the liquid helium) and the liquid helium is returned to the reservoir to provide further cooling. In this manner the system may be used in a "lossless" state whereby effectively no helium is lost from the system during operation, since all helium which is boiled-off is ultimately recondensed by the PTR. The heat pipe is shown at 616, connected to the first and second stages of the PTR by respective high thermal links as described above.

As cryocoolers, such as PTRs, improve over time in terms of their cooling power it is becoming possible to reduce the amount of cryogen needed to ensure reliable operation of superconducting magnets. For example rather than immerse the material in a bath of effectively static fluid it is conceivable to use an externally pumped circuit to provide flowing cryogen so as to cool the superconductor. This causes technical challenges in terms of engineering such a flow path which provides sufficient heat sinking of all parts of the magnet. Furthermore, whilst liquid coolant may be preferred, it is possible, particularly for high temperature superconductors, to consider gaseous cooling (since the superconducting transition temperature is above the boiling point of the liquid cryogen). A cooling system embodying such a pumped flow path, where part of the flow circuit is cooled using a cryocooler, is contemplated as an alternative example cooling system 613.

At the forefront of such developments is the desire to deliver the cooling power directly from a cryocooler to the magnet coils using conductive cooling through a solid high thermal conductivity material, rather than use cryogenic fluids. Some such designs have been proposed and in these cases it is particularly important to provide a close approach between the cooled stage of the cryocooler, such as the second stage 615*b* of a PTR, and the superconducting material. In principle this may also be achieved using the cooling system 613. It may be necessary in practice to provide multiple instances of the cryocooler such as PTR 614 in the above examples, particularly in the conductive cooling case here.

In each of the above examples of providing cooling power to the superconducting material there is advantage in decreasing the cooling time such that the "downtime" between MRI processes is reduced. This is particularly important in busy environments such as hospitals. It will therefore be appreciated that by the use of a PTR according to the present invention having increased cooldown speed provides a significant advantage when implemented in an MRI system.

Whilst the above discussion is focussed upon the cooling of the primary magnet system 601, it has been proposed that cryocoolers may be useful in the cooling of other parts of an MRI system. For example, it has been proposed that an RF transmitter/receiver system may be implemented using coils which are cooled. These may be implemented as superconducting coils in which case they require to be cooled below their superconducting transition temperature. The improved PTR systems discussed herein may also be used to advantage in the cooling of such coils (either resistive or superconducting), for example by cooling a flow path of circulating coolant which may be at cryogenic temperature.

The invention claimed is:

1. A cryogenic cooling apparatus comprising:
   a supply gas line and a return gas line adapted to be coupled to a compressor when in use;
   a coupling element in gaseous communication with the supply and return gas lines, the coupling element being adapted in use to supply gas to a mechanical refrigerator, the pressure of said supplied gas being modulated by the coupling element in a cyclical manner;
   a sensing system adapted to monitor the operational state of the mechanical refrigerator when in use; and,
   a control system adapted to modulate the frequency of a cyclical gas pressure supplied by the coupling element in accordance with the monitored operational state;
   wherein the mechanical refrigerator comprises:
   a first cooled stage and a second cooled stage, the second cooled stage being adapted to be coupled thermally with a target apparatus to be cooled; and,
   a selectively coupleable thermal link in the form of a heat pipe for thermally coupling the first cooled stage of the mechanical refrigerator to the second cooled stage in dependence upon the operational state of the mechanical refrigerator;
   wherein the heat pipe has a first part coupled thermally to the first stage of the mechanical refrigerator and a second part coupled thermally to the second stage of the mechanical refrigerator, the heat pipe being adapted to contain a condensable gaseous coolant when in use;
   the cryogenic cooling apparatus being adapted in use to be operated in a first cooling mode in which the temperature of the cooled member causes the coolant within the second part of the heat pipe to be gaseous and the temperature of the first stage causes the coolant in the first part to condense, whereby the cooled member is cooled by the movement of the condensed liquid from the first part to the second part of the heat pipe;
   wherein the sensing system is configured to detect when the apparatus is in the first cooling mode and wherein the control system is further adapted to modulate the frequency of the cyclical gas pressure during a cool down procedure in response to the sensing system detecting that the first cooling mode has begun, wherein the modulation reduces the cooling power of the first cooled stage so as to prolong the first cooling mode.

2. Apparatus according to claim 1, wherein the sensing system comprises a pressure sensing apparatus adapted to monitor the pressure in at least one of the supply and return gas lines.

3. Apparatus according to claim 1, wherein the apparatus further comprises a temperature sensing apparatus for monitoring a temperature within a cooled region of the mechanical refrigerator and wherein the control system is further adapted to control the frequency of the cyclical gas pressure in accordance with the temperature monitored by the temperature sensing apparatus.

4. Apparatus according to claim 1, wherein the sensing system comprises a temperature sensing apparatus adapted to monitor the temperature in one or more of the first cooled stage, the second cooled stage or the thermal link.

5. Apparatus according to claim 1, wherein the modulation increases the cooling power of the second cooled stage.

6. Apparatus according to claim 1, wherein the thermal link is arranged to be operable under the control of the control system.

7. Apparatus according to claim 1, wherein the modulation reduces the rate of cooling of the first cooled stage during the first cooling mode.

8. Apparatus according to claim 1, wherein the apparatus is further adapted in use to be operated in an second cooling mode in which the temperature of the first cooled stage causes the freezing of the coolant at the first part and causes the temperature of the second cooled stage to then become lower than the temperature of the first cooled stage.

9. Apparatus according to claim 8, wherein the sensing system is configured to detect when the second cooling mode has begun and wherein the control system is configured to modulate the frequency of the cyclical gas pressure in response to the sensing system detecting that the first cooling mode has ended and the second cooling mode has begun.

10. Apparatus according to claim 1, wherein the sensing system comprises a thermocouple configured to monitor the temperature of the heat pipe in order to detect when the apparatus is in the first cooling mode.

11. Apparatus according to claim 9, wherein the control system comprises a heater in thermal communication with the heat pipe for use in controlling the environment in the heat pipe.

12. Apparatus according to claim 1, further comprising a coolant gas or mixture of gases sealed within the heat pipe.

13. Apparatus according to claim 12, wherein the coolant comprises one or more gases selected from the group of: Nitrogen, Oxygen, Xenon, Argon, Krypton, Carbon Dioxide, Hydrogen.

14. Apparatus according to claim 1, further comprising an external volume in fluid communication with the interior of the heat pipe.

15. Apparatus according to claim 1, wherein the heat pipe comprises an internal volume for containing the coolant, and which contains the first and second parts in fluid communication with one another.

16. Apparatus according to claim 1, wherein the heat pipe comprises walls within which are positioned bellows so as to act as a vibration-dampening mechanism.

17. Apparatus according to claim 1, wherein the heat pipe may further comprise an anti-radiation member operative to reduce the passage of electromagnetic radiation between the first and second parts, the anti-radiation member being arranged to allow passage of liquid from one side of the member to the opposing side.

18. Apparatus according to claim 1 wherein the mechanical refrigerator comprises an additional cooled stage, the additional stage being either an intermediate stage between the first and second stages, or being a third stage.

19. Apparatus according to claim 1, further comprising target apparatus, thermally coupled to the stage of the refrigerator which is capable of attaining the lowest operational temperature, the thermal coupling being through a high thermal conductivity member.

20. Apparatus according to claim 1, wherein the coupling element comprises a rotary valve.

21. Apparatus according to claim 1, wherein the coupling element is driven by a motor and wherein the control system is further adapted to control the speed of the motor.

22. Apparatus according to claim 1, wherein the mechanical refrigerator is selected from the group of: a pulse tube refrigerator, a Gifford-McMahon refrigerator, a Stirling refrigerator.

23. Use of an apparatus according to claim 1 in providing cooling for a magnetic resonance system.

24. Apparatus according to claim 1, wherein said compressor is in gaseous communication with the supply and return gas lines.

25. A system according to claim 24, wherein the compressor is selected from the group of a: scroll compressor, rotary screw compressor, rotary vane compressor, rotary lube compressor or diaphragm compressor.

26. Use of a cryogenic cooling system according to claim 24 in providing cooling for a magnetic resonance system.

27. A magnetic resonance system comprising:
a magnet system comprising a number of magnets for generating a magnetic field which is suitable for obtaining magnetic resonance signals from a target region;
a radio frequency system for obtaining radio frequency signals from the target region;
a control system for controlling the magnetic fields experienced within different parts of the target region in accordance with the magnet system and radio frequency system;
a processing system for forming an image from the radio frequency signals; and,
a cooling system adapted in use to cool one or more of the magnet system or radio frequency systems using a cryogenic cooling apparatus according to claim 1.

28. A magnetic resonance system according to claim 27, wherein the magnet system includes superconductive magnets and wherein the cryogenic cooling system further comprises a heat transfer medium which is arranged to act as a heat sink for the superconductive magnets and wherein the cryogenic cooling apparatus is operative to extract heat from the heat transfer medium when in use.

29. A method of controlling an apparatus in accordance with claim 1, the method comprising:

monitoring the operational state of the mechanical refrigerator using the sensing system; and,
modulating the frequency of the cyclical gas pressure supplied by the coupling element in accordance with the monitored state.

30. A method according to claim 29, wherein the said step of monitoring comprises monitoring one or each of: the pressure in at least one of the supply and return gas lines, or the temperature within the mechanical refrigerator.

31. A method according to claim 22, wherein the coupling element is moveable in a rotational manner and wherein the frequency is effected by moving the coupling element at a corresponding rotational speed.

32. A method according to claim 30, wherein the frequency is modulated in accordance with a predetermined relationship.

33. A method according to claim 30, wherein the frequency is modulated so as to maintain the monitored pressure within a predetermined pressure range.

34. A method according to claim 33, wherein the predetermined pressure range is set in accordance with a maximum operational pressure of the apparatus.

35. A method according to claim 34, wherein if, in accordance with the predetermined relationship, the frequency would be below a minimum threshold frequency then the frequency is set to the minimum threshold frequency.

36. A method according to claim 30, wherein if, in accordance with the predetermined relationship, the frequency would be above a maximum threshold frequency then the frequency is set to the maximum threshold frequency.

37. A method according to claim 30, wherein the frequency is in the range 1 to 5 Hz.

38. A method according to claim 30, wherein the monitored pressure is in the range 1 to 40 MPa.

39. A method according to claim 30, wherein the coupling element is driven by a motor and wherein the method comprises controlling the motor speed to so as to control the frequency.

40. A method according to claim 30, wherein the supplied gas is helium.

41. A method according to claim 30, further comprising using the sensing system to monitor the temperature in one or more of the first cooled stage, the second cooled stage or the thermal link and maintaining the operation of the thermal link by either reducing the cooling power applied to the first cooled stage or by locally heating one or more of: the thermal link or the first cooled stage.

42. A method according to claim 41, wherein when the said maintaining of the operation of the thermal link is provided by reducing the cooling power applied to the first stage, the method comprises the system controller modifying the frequency of the cyclical gas pressure supplied by the coupling element.

43. A method according to claim 42, wherein the modified frequency is a constant frequency.

44. A method according to claim 41, wherein the step of maintaining of the operation of the thermal link is dependent upon the monitored temperature being within a predetermined temperature range.

45. A method according to claim 41, wherein the sensing system is adapted to indirectly sense the temperature by monitoring of one or more pressures within the mechanical refrigerator.

46. A method of controlling an apparatus in accordance with claim 7, the method comprising:

i) monitoring the operational state of the mechanical refrigerator using the sensing system;
ii) modulating the frequency of the cyclical gas pressure supplied by the coupling element in accordance with the monitored state;
iii) providing a predetermined quantity of coolant to the interior of the heat pipe;
iv) causing the second cooled stage to adopt a temperature sufficient to ensure the coolant within the second part of the heat pipe is in the gaseous phase;
v) operating the mechanical refrigerator to cause the first stage of the mechanical refrigerator to adopt a temperature which causes the coolant within the first part of the heat pipe to condense; and,
vi) cooling the second cooled stage by causing the movement of the condensed coolant from the first part to the second part of the heat pipe.

47. A method according to claim 46, further comprising:
vii) operating the mechanical refrigerator after step (vi) to cause the first stage of the mechanical refrigerator to adopt a temperature which causes the coolant within the first part of the heat pipe to freeze; and,
viii) further operating the mechanical refrigerator such that the second stage cools to an operational temperature lower than that of the first stage for using in cooling the target apparatus.

48. A method of controlling a magnetic resonance system in accordance with claim 27, the method comprising:
controlling the cryogenic cooling apparatus to cool one or more of the magnet system or radio frequency systems to a working temperature;
providing at least one radio frequency signal in order to obtain radio frequency signals from the target region;
controlling the magnetic fields produced by the magnet system in accordance with a desired imaging location of the target region; and,
processing the obtained radio frequency signals in order to form an image of the desired imaging location of the target region.

* * * * *